United States Patent
Kubo et al.

[11] Patent Number: 5,496,835
[45] Date of Patent: Mar. 5, 1996

[54] HETEROCYCLIC COMPOUNDS HAVING ANGIOTENSIN II ANTAGONISTIC ACTIVITY AND USE THEREOF

[75] Inventors: Keiji Kubo, Osaka; Yoshiyuki Inada, Kawanishi; Takehiko Naka, Kobe, all of Japan

[73] Assignee: Takeda Chemical Industries, Ltd., Osaka, Japan

[21] Appl. No.: 171,164

[22] Filed: Dec. 22, 1993

[30] Foreign Application Priority Data

Dec. 22, 1992 [JP] Japan .................. 4-342917

[51] Int. Cl.⁶ .................. C07D 413/10; A61K 31/41
[52] U.S. Cl. .................. 514/361; 514/364; 548/136; 548/144
[58] Field of Search .................. 548/129, 132; 514/361, 364

[56] References Cited

U.S. PATENT DOCUMENTS 5,243,054  9/1993  Naka .................. 548/132

FOREIGN PATENT DOCUMENTS

| | | |
|---|---|---|
| 0432737 | 6/1991 | European Pat. Off. . |
| 0446062 | 9/1991 | European Pat. Off. . |
| 0501892 | 9/1992 | European Pat. Off. . |
| 0507594 | 10/1992 | European Pat. Off. . |
| 0520423 | 12/1992 | European Pat. Off. . |
| 0519831 | 12/1992 | European Pat. Off. . |
| 9115209 | 10/1991 | WIPO . |
| 9115479 | 10/1991 | WIPO . |

*Primary Examiner*—Robert Gerstl
*Attorney, Agent, or Firm*—Foley & Lardner

[57] ABSTRACT

This invention relates to a compound represented by the formula

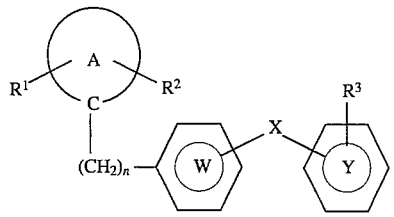

wherein the ring A stands for a 5–10 membered aromatic heterocyclic group optionally having, besides $R^1$ and $R^2$, further substituents; $R^1$ stands for an optionally substituted hydrocarbon residue which is optionally bonded through a hetero-atom; $R^2$ stands for a group capable of liberating proton in a living body or a group convertible thereinto; $R^3$ stands for an 5–7 membered optionally substituted heterocyclic residue having, as a group capable of constituting the ring, carbonyl group, thiocarbonyl group, an optionally oxidized sulfur atom or a group convertible into them; X shows that the ring Y and the ring W are bonded to each other directly or through a spacer having an atomic length of two or less; the ring W and the ring Y are each an optionally substituted aromatic hydrocarbon or aromatic heterocyclic residue; and n denotes an integer of 1 to 3, or a salt thereof and to an angiotensin II antagonistic agent containing the compound (I) or a salt thereof.

18 Claims, No Drawings

HETEROCYCLIC COMPOUNDS HAVING ANGIOTENSIN II ANTAGONISTIC ACTIVITY AND USE THEREOF

FIELD OF THE INVENTION

This invention relates to novel heterocyclic compounds having excellent pharmacological actions and their use.

More specifically, the present invention relates to compounds represented by the formula

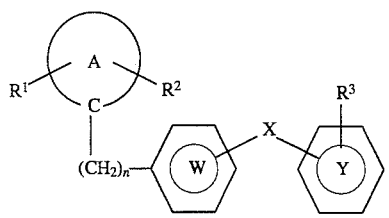

wherein the ring A stands for a 5–10 membered aromatic heterocyclic group optionally having, besides $R^1$ and $R^2$, further substituents; $R^1$ stands for an optionally substituted hydrocarbon residue which is optionally bonded through a hetero-atom; $R^2$ stands for a group capable of liberating proton in a living body or a group convertible thereinto; $R^3$ stands for an optionally substituted 5–7 membered heterocyclic residue having, as a group capable of constituting the ring, carbonyl group, thiocarbonyl group, an optionally oxidized sulfur atom or a group convertible into them; X shows that the ring Y and the ring W are bonded to each other directly or through a spacer having an atomic length of two or less; the ring W and the ring Y are each an optionally substituted aromatic hydrocarbon or aromatic heterocyclic residue; and n denotes an integer of 1 to 3, or a salt thereof and further to an angiotensin II antagonist containing them, which have a strong angiotensin II antagonistic action and antihypertensive action and useful as therapeutic agents of circulatory diseases such as hypertension, heart diseases (hypercardia, cardiac insufficiency, myocardial infarction, etc.), nephritis and cerebral apoplexy, and as agents for improving cerebral function.

Additionally, the use of such compounds and compositions thereof as diagnostic agents for the aforementioned diseases is also contemplated.

BACKGROUND OF THE INVENTION

The renin-angiotensin system is involved in the homeostatic function to control systemic blood pressure, the volume of body fluid, balance among the electrolytes, etc., associated with the aldosterone system. Relation between the renin-angiotensin system and hypertension has been clarified by the development of angiotensin II (AII) converting enzyme inhibitors (ACE inhibitors) which prevent ACE from producing angiotensin II having a strong vasoconstrictive action. Since angiotensin II constricts blood vessel to elevate blood pressure via the angiotensin II receptors on the cellular membranes, angiotensin II antagonists, like the ACE inhibitors, can be used for the therapy of hypertension caused by angiotensin II. It has been reported that a number of angiotensin II analogues such as saralasin, $(Sar^1, Ile^8)AII$ and the like possess potent angiotensin II antagonism. It has, however, been reported that, when peptide antagonists are administered non-orally, their actions are not prolonged and, when administered orally, they are ineffective (M. A. Ondetti and D. W. Cushman, Annual Reports in Medicinal Chemistry, 13, 82–91 (1978)).

On the other hand, for solving the problems observed in these peptide angiotensin II antagonists, studies on non-peptide angiotensin II antagonists have been developed. In the earliest studies in this field, imidazole derivatives having angiotensin II antagonism have been disclosed in JPA S56(1981)-71073, S56(1981)-71074, S57(1982)-98270 and S58(1983)-157768, U.S. Pat. No. 4,355,040 and 4,340,598, etc. Later, improved imidazole derivatives are disclosed in EP-0253310, EP-0291969, EP-0324377, EP-403158, WO-9100277, JPA S63(1988)-23868 and JPA H1(1989)-117876; pyrazole derivatives in EP-0409332, EP-0446062 and WO-9115479; pyrrole and triazole derivatives in EP-0323841 and JPA H1(1989)-287071; benzimidazole derivatives in U.S. Pat. No. 4,880,804, EP-0392317, EP-0399732, EP-0400835 and JPA H3(1991)-63264; azaindene derivatives in EP-0399731; pyrimidone derivatives in EP-0407342; pyrimidine derivatives in WO-9115209; pyridine derivatives in EP-0475206 and EP-0499415; quinazolinone derivatives in EP-0411766; and quinoline derivatives in EP-050794 as angiotensin II antagonists.

However, in order to become a practically useful therapeutic agent, angiotensin II antagonists are required to have a strong and long-lasting angiotensin II antagonistic action by oral administration. As shown in so far known literature references, the preferable structural feature as strong angiotensin II antagonists is considered to have an acid group, for example, tetrazole group or carboxyl group on the biphenyl side chain, especially tetrazole group as most preferable one and clinical test of compounds having the tetrazole group for anti-hypertension agents is conducted (Y. Christen, B. Waeber, J. Nussberger, R. J. Lee, P.B.M.W.M. Timmermans, and H. R. Brunner, Am. J. Hypertens., 4, 350S (1991)). However, compounds having tetrazole ring and azide compounds to be used for synthesizing them have been known as involving a danger of explosion, which becomes a serious problem to the large scale preparation and industrial production.

OBJECT OF THE INVENTION

The present invention is to provide novel cyclic compounds having a heterocyclic residue substitutable for an acid group such as tetrazole or carboxylic group, which have a strong angiotensin II antagonistic action and antihypertensive action and which can be put to practical use satisfactorily as medicinal agents.

SUMMARY OF THE INVENTION

The present inventors considered that compounds acting to control renin-angiotensin system as well as being clinically useful for the treatment of circulatory diseases such as hypertension, cardiopathy (hypercardia, heart failure, cardiac infarction, etc.), cerebral apoplexy, and improving cerebral function, are required to have an angiotensin II receptor antagonistic activity and also have a strong and long-lasting angiotensin II antagonistic activity and hypotensive action by oral administration, and they have made extensive and intensive studies.

As a result, the present inventors have found that novel cyclic compounds (I) have a potent angiotensin II receptor antagonistic activity as well as a long-lasting and strong AII antagonistic and antihypertensive actions by oral administration. The present inventors have further developed studies to accomplish the present invention.

More specifically, the present invention relates to (1) compounds represented by the formula (I)

[Structural formula showing ring A with substituents $R^1$, $R^2$, C, $(CH_2)_n$, W, X, $R^3$, Y]

wherein the ring A stands for a 5–10 membered aromatic heterocyclic group optionally having, besides $R^1$ and $R^2$, further substituents; $R^1$ stands for an optionally substituted hydrocarbon residue which is optionally bonded through a hetero-atom; $R^2$ stands for a group capable of liberating proton in a living body or a group convertible thereinto; $R^3$ stands for an optionally substituted 5–7 membered heterocyclic residue having, as a group capable of constituting the ring, carbonyl group, thiocarbonyl group, an optionally oxidized sulfur atom or a group convertible into them; X shows that the ring Y and the ring W are bonded to each other directly or through a spacer having an atomic length of two or less; the ring W and the ring Y are each an optionally substituted aromatic hydrocarbon or aromatic heterocyclic residue; and n denotes an integer of 1 to 3, or salts-thereof, and (2) to an angiotensin II antagonistic agent containing the compound (I) or a salt thereof.

DETAILED DESCRIPTION OF THE INVENTION

Referring to the above-mentioned formula (I), the ring A is a 5- to 10-membered (preferably 5-, 6-, 8-, 9- or 10-membered) aromatic heterocyclic ring having at least one unsaturated bond, which may be a monocyclic or condensed ring. And, as preferable positions at which the substituents $R^1$ and $R^2$ on the ring A are bonded, when the ring A is monocyclic, mention is made of positions adjacent to the carbon atom to which a group shown by —$(CH_2)n$- is bonded; when the ring A is condensed one, $R^1$ is preferably bonded at the position adjacent to the carbon atom to which the group shown by —$(CH_2)n$- is bonded, and $R^2$ is preferably bonded at the peri-position of the said carbon atom, but not to be specifically limited thereto. Typical examples of these heterocyclic groups and of preferable positions to which $R^1$ and $R^2$ are bonded respectively are shown below,

[Structural formulas of various heterocyclic rings with $R^1$ and $R^2$ substituents]

wherein $R^1$ and $R^2$ are of the same meaning as defined above, and it is needless to say that they should not be limited thereto.

Examples of the hydrocarbon residue represented by $R^1$ include alkyl, alkenyl, alkynyl, cycloalkyl, aryl and aralkyl groups. Among them, alkyl, alkenyl and cycloalkyl groups are preferable. The hydrocarbon residue may be bonded to the ring A through a hetero atom.

The alkyl group represented by $R^1$ is a straight-chain or branched lower alkyl group having 1 to about 8 carbon atoms, as exemplified by methyl, ethyl, propyl isopropyl, butyl, isobutyl, sec-butyl, t-butyl, pentyl, i-pentyl, hexyl, heptyl or octyl.

The alkenyl group represented by $R^1$ is a straight-chain or branched lower alkenyl group having 2 to about 8 carbon atoms, as exemplified by vinyl, propenyl, 2-butenyl, 3-butenyl, isobutenyl or 2-octenyl.

The alkynyl group represented by $R^1$ is a straight-chain or branched lower alkynyl group having 2 to about 8 carbon atoms, as exemplified by ethynyl, 2-propinyl, 2-butynyl, 2-pentynyl or 2-octynyl.

The cycloalkyl group represented by $R^1$ is a lower cycloalkyl group having 3 to about 6 carbon atoms, as exemplified by cyclopropyl, cyclobutyl, cyclopentyl or cyclohexyl.

The above-mentioned alkyl, alkenyl, alkynyl or cycloalkyl group may optionally be substituted with hydroxyl group, an optionally substituted amino group (e.g. amino, N-lower ($C_{1-4}$) alkylamino or N,N-di-lower ($C_{1-4}$)alkylamino), halogen, a lower ($C_{1-4}$) alkoxy group, or a lower ($C_{1-4}$) alkylthio group.

The aralkyl group represented by $R^1$ is, for example, a phenyl-lower ($C_{1-4}$) alkyl such as benzyl or phenethyl, and the aryl group represented by $R^1$ is, for example, phenyl.

The above-mentioned aralkyl or aryl group may optionally have, on an optional position of its benzene ring, for example, halogen (e.g. F, Cl or Br), nitro, an optionally substituted amino group (e.g. amino, N-lower ($C_{1-4}$) alkylamino or N,N-di-lower ($C_{1-4}$) alkylamino), lower ($C_{1-4}$) alkoxy (e.g. methoxy or ethoxy), lower ($C_{1-4}$) alkylthio (e.g. methylthio or ethylthio) or lower ($C_{1-4}$) alkyl (e.g. methyl or ethyl).

Among the above-exemplified groups represented by $R^1$, optionally substituted alkyl, alkenyl or cycloalkyl groups (e.g. a lower ($C_{1-5}$) alkyl, lower ($C_{2-5}$) alkenyl or lower ($C_{3-6}$) cycloalkyl group optionally substituted with hydroxyl group, amino group, halogen or a lower ($C_{1-4}$) alkoxy group) are preferable.

The above-mentioned $R^1$ may optionally be bonded through a hetero-atom (e.g. nitrogen ($N(R^9)$ ($R^9$ stands for hydrogen or a lower ($C_{1-4}$) alkyl)), oxygen or sulfur (—S(O)m— (m denotes an integer of 0 to 2)), etc.), and, among them, optionally substituted alkyl or alkenyl group bonded through a hetero-atom (e.g. methylamino, ethylamino, propylamino, propenylamino, isopropylamino, allylamino, butyrylamino, isobutyrylamino, dimethylamino, methylethylamino, methoxy, ethoxy, propoxy, isopropoxy, propenyloxy, allyloxy, butoxy, isobutoxy, sec-butoxy, t-butoxy, 2-butenyloxy, 3-butenyloxy, isobutenyloxy, pentoxy, isopentoxy, hexyloxy, methylthio, ethylthio, propylthio, isopropylthio, allylthio, butylthio, isobutylthio, secbutylthio, t-butylthio, 2-butenylthio, 3-butenylthio, isobutenylthio, pentylthio, isopentylthio, hexylthio, etc.) are preferable.

Examples of the group $R^2$ capable of liberating proton or a group convertible thereinto in vivo include optionally esterified or amidated carboxyl, tetrazolyl, trifluoromethanesulfonic acid amide (—NHSO$_2$CF$_3$), phosphoric acid and sulfonic acid groups. These groups may optionally be protected with an optionally substituted lower alkyl group or acyl group, and may be any one if only they are capable of liberating proton under biological or physiological conditions (for example, in vivo reaction such as oxidation, reduction or hydrolysis by .in vivo enzymes) or a group convertible thereinto.

Examples of optionally esterified or amidated carboxyl represented by $R^2$ include groups represented by the formula —CO-D [wherein D stands for hydroxyl group, optionally substituted amino (e.g. amino, N-lower ($C_{1-4}$) alkylamino, and N,N-di-lower ($C_{1-4}$) alkylamino) or optionally substituted alkoxy {e.g. a lower ($C_{1-6}$) alkoxy group, whose alkyl moiety is optionally substituted with hydroxyl group, optionally substituted amino (e.g. amino, dimethylamino, diethylamino, piperidino and morpholino), halogen, lower ($C_{1-6}$) alkoxy, lower ($C_{1-6}$) alkylthio or optionally substituted dioxolenyl (e.g. 5-methyl-2-oxo-1,3-dioxolen-4-yl), or group represented by the formula —O—CH($R^4$)—OCOR$^5$ [wherein $R^4$ stands for hydrogen, a $C_{1-6}$ straight-chain or branched lower alkyl group (e.g. methyl, ethyl, n-propyl, isopropyl, n-butyl, isobutyl, t-butyl, n-pentyl, isopentyl and neopentyl), a $C_{2-6}$ straight-chain or branched lower alkenyl group or a $C_{3-8}$ cycloalkyl group (e.g. cyclopentyl, cyclohexyl and cycloheptyl), and $R^5$ stands for a $C_{1-6}$ straight-chain or branched lower alkyl group (e.g. methyl, ethyl, n-propyl, isopropyl, n-butyl, isobutyl, sec-butyl, t-butyl, n-pentyl, isopentyl and neopentyl), a $C_{2-6}$ straight-chain or branched lower alkenyl group, a $C_{3-8}$ cycloalkyl group (e.g. cyclopentyl, cyclohexyl and cycloheptyl), a $C_{1-3}$ lower alkyl group substituted with $C_{3-8}$ cycloalkyl (e.g. cyclopentyl, cyclohexyl and cycloheptyl) or an optionally substituted aryl group such as phenyl (e.g. benzyl, p-chlorobenzyl, phenethyl, cyclopentylmethyl and cyclohexylmethyl), a $C_{2-3}$ lower alkenyl group optionally substituted with $C_{3-8}$ cycloalkyl or an optionally substituted aryl group such as phenyl (e.g. cinnamyl, etc. having alkenyl moiety such as vinyl, propenyl, ally, and isopropenyl), an aryl group such as optionally substituted phenyl (e.g. phenyl, p-tolyl, naphthyl), a $C_{1-6}$ straight-chain or branched lower alkoxy group (e.g. methoxy, ethoxy, n-propoxy, isopropoxy, n-butoxy, isobutoxy, sec-butoxy, t-butoxy, n-pentyloxy, isopentyloxy and neopentyloxy), a $C_{2-8}$ straight-chain or branched lower alkenyloxy group (e.g. allyloxy and isobutenyloxy), a $C_{3-8}$ cycloalkyloxy group (e.g. cyclopentyloxy, cyclohexyloxy and cycloheptyloxy), a $C_{1-3}$ lower alkoxy group substituted with $C_{3-8}$ cycloalkyl (e.g. cyclopentyl, cyclohexyl and cycloheptyl) or an aryl group such as optionally substituted phenyl (e.g. benzyloxy, phenethyloxy, cyclopentylmethyloxy and cyclohexylmethyloxy having alkoxy moiety such as methoxy, ethoxy, n-propoxy and isopropoxy), a $C_{2-3}$ lower alkenyloxy group substituted with $C_{3-8}$ cycloalkyl (e.g. cyclopentyl, cyclohexyl and cycloheptyl) or an aryl group such as optionally substituted phenyl (e.g. cinnamyloxy having alkenyloxy moiety such as vinyloxy, propenyloxy, allyloxy, isopropenyloxy) and an aryloxy group such as optionally substituted phenoxy (e.g. phenoxy, p-nitrophenoxy and naphthoxy)]}]. And, examples of the substituent represented by $R^2$ may also include a group capable of liberating proton or a group convertible thereinto in vivo (e.g. tetrazolyl, trifluoromethanesulfonic acid amide, phosphoric acid or sulfonic acid optionally protected with alkyl (e.g. a lower ($C_{1-4}$) alkyl) or acyl (e.g. lower ($C_{2-5}$) alkanoyl and optionally substituted benzoyl).

Examples of the substituent $R^2$ include —COOH and a salt thereof, —COOMe, —COOEt, —COOtBu, —COOPr, pivaloyloxymethoxycarbonyl, 1-(cyclohexyloxycarbonyloxy)ethoxycarbonyl, 5-methyl-2-oxo-1,3-dioxolen-4-ylmethoxycarbonyl, acetoxymethyloxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1-(acetyloxy)ethoxycarbonyl, 1-(isobutyryloxy)ethoxycarbonyl, cyclohexylcarbonyloxymethoxycarbonyl, benzoyloxymethoxycarbonyl, cinnamyloxycarbonyl and cyclopentylcarbonyloxymethoxycarbonyl. As such groups as above, mention is made of any one capable of liberating proton or a group convertible thereinto under biological or physiological conditions (e.g. in vivo reaction such as oxidation, reduction or hydrolysis catalyzed by in vivo enzymes). $R^2$ may be carboxyl group or a prodrug thereof. $R^2$ may also be groups convertible into anion in vivo, biologically or chemically.

And, a compound, in which $R^2$ is a group capable of liberating proton or a group convertible thereinto (e.g. optionally protected carboxyl group, tetrazolyl group, carbaldehyde group and hydroxymethyl group; and cyano group) chemically (e.g. oxidation, reduction or hydrolysis), is useful as synthetic intermediate.

Among the groups described as $R^2$, preferable ones include carboxyl, esterified carboxyl (e.g. methyl ester, ethyl ester or an ester formed by bonding of a group represented by the above-mentioned formula —O—CH($R^4$)—OCOR$^5$ to carbonyl) and optionally protected tetrazolyl, carboaldehyde and hydroxymethyl.

The ring A may optionally have, besides the groups represented by $R^1$, $R^2$ and —(CH$_2$)n-, further substituents represented by Q, as exemplified by halogen (e.g. F, Cl, Br), nitro, cyano, an optionally substituted amino group [e.g. amino, N-lower ($C_{1-4}$) alkylamino (e.g. methylamino), N,N-dilower ($C_{1-4}$) alkylamino (e.g. dimethylamino), N-arylamino (e.g. phenylamino), alicyclic amino (e.g. morpholino, piperidino, piperazino and N-phenylpiperazino)], groups represented by the formula —U—$R^6$ [wherein U stands for a bond, —O—, —S— or —CO—, and $R^6$ stands for hydrogen, an optionally substituted lower alkyl group (e.g. a lower ($C_{1-4}$) alkyl optionally substituted with hydroxyl group, an optionally substituted amino group (e.g. amino), halogen, nitro, cyano or a lower ($C_{1-4}$) alkoxy), an optionally substituted phenyl group (e.g. phenyl group optionally substituted with hydroxyl group, an optionally substituted amino group (e.g. amino, N-lower ($C_{1-4}$) alkylamino (e.g. methylamino), N,N-di-lower ($C_{1-4}$) alkylamino (e.g. dimethylamino), acylamino (e.g. acetylamino), etc.), halogen, nitro, cyano, a lower ($C_{1-4}$) alkyl group, a lower ($C_{1-4}$) alkoxy group, a lower ($C_{1-4}$) alkylthio group, acyl group (e.g. acetyl group)) or the like]. One or two of these substituents may optionally be substituted simultaneously on optional positions of the ring.

Among aromatic heterocyclic rings as the ring A, those having pyrazole, pyridine, pyrimidine, quinoline or isoquinoline (especially pyrazole, pyridine) skeleton are preferable.

As optionally substituted aromatic hydrocarbon residues or aromatic heterocyclic residues represented by the ring Y and the ring W, mention is made of an aromatic hydrocarbon residue such as benzene ring, and 4- to 7-membered monocyclic or condensed heterocyclic residues containing one or not less than two of N, S and O in pyridine, pyrimidine, pyridazinyl, pyrazine, thiophene, furan, pyrrole, imidazole, pyrazole, isothiazole, isoxazole, benzofuran, isobenzofuran, indolizine, isoindole, 3H-indole, indole, 1H-indazole, purine, 4H-quinolizine, isoquinoline, quinoline, phthalazine, naphthylizine, quinoxaline, quinazolyne, cinnoline and pteridine ring, and, as preferable example, benzene ring is mentioned.

The above-mentioned aromatic hydrocarbon residues or aromatic heterocyclic residues represented by the ring Y have substituents represented by $R^3$. Examples of the substituents represented by $R^3$ include, as shown below, 5- to 7-membered (preferably 5- to 6-membered) monocyclic optionally substituted heterocyclic residues containing one or not less than two of N, S and O (preferably N-containing heterocyclic residue having hydrogen atom capable of converting to proton) or groups convertible thereinto. For example, mention is made of;

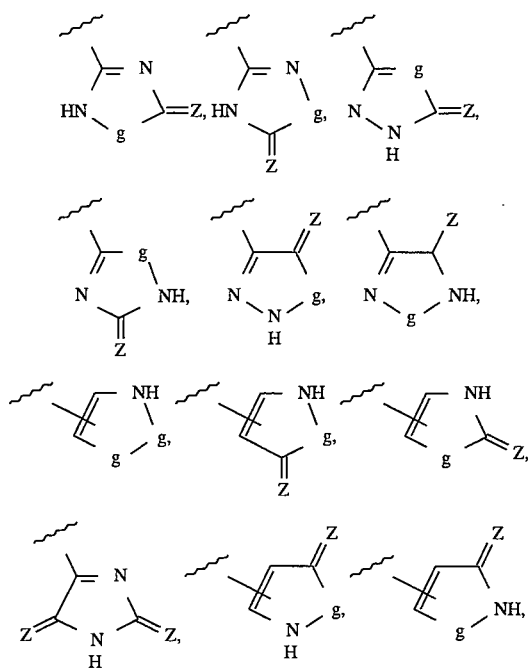

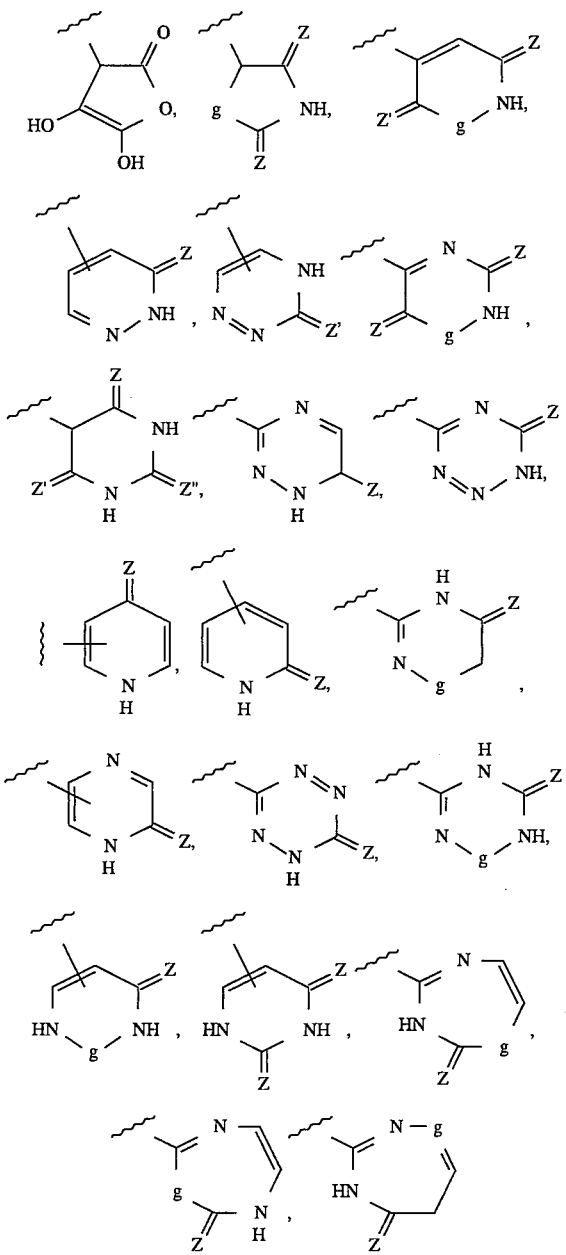

Or, the bonding of the group represented by $R^3$ and optionally substituted aromatic hydrocarbon residue or aromatic heterocyclic residue represented by the ring Y includes not only C—C bondage as shown above but also the bonding through one of the plural nitrogen atoms existing in such a case as g=—NH— in the above formulae. For example, when $R^3$ stands for a group

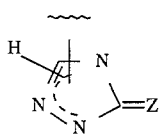

it stands for

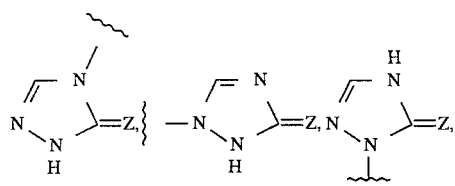

or

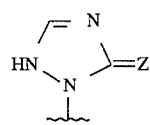

Other examples of $R^3$ bonding through nitrogen atom include

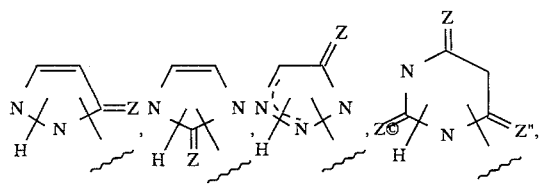

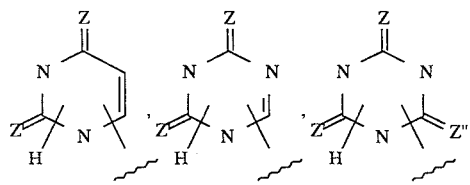

[In the above formulae, g stands for —$CH_2$—, —$NR^9$—, O

>=Z, >=Z' and >=Z" respectively stand for carbonyl group, thiocarbonyl group or an optionally oxidized sulfur atom (e.g. S, S(O), S(O)$_2$, etc.), preferably carbonyl or thiocarbonyl group, more preferably carbonyl; m denotes 0, 1 or 2; and $R^9$ stands for hydrogen atom or an optionally substituted lower alkyl group].

Preferable examples of $R^3$ include 2,5-dihydro-5-oxo-1, 2,4-oxadiazole ring residue, 2,5-dihydro-5-thioxo-1,2,4-thiadiazole ring residue or 2,5-dihydro-5-oxo-1,2,4-thiadiazole ring residue having —NH or —OH group as proton donor and carbonyl group, thiocarbonyl group or sulfinyl group as proton acceptor simultaneously.

And, while the heterocyclic residue shown by $R^3$ may form a condensed ring by the bondage of the substituent on the ring, it is preferably a 5- to 6-membered ring, more preferably a 5-membered heterocyclic residue. Especially, groups represented by the formula

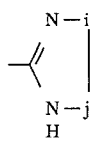

wherein i stands for —O— or —S—; j stands for >=O, >=S or >S(O)$_m$; and m is of the same meaning as defined above, (especially 2,5-dihydro-5-oxo-1,2,4-oxadiazol-3-yl, 2,5-dihydro-5-thioxo-1,2,4-oxadiazol-3-yl, 2,5-dihydro-5oxo-1, 2,4-thiadiazol-3yl) are preferable. The substitution position of $R^3$ is, when the ring Y is phenyl for example, any one of ortho-, meta- and para-positions, and, among them, orthoposition is preferable.

And, while the above-mentioned heterocyclic residues ($R^3$) include three tautomers (a, b and c) as shown below, in 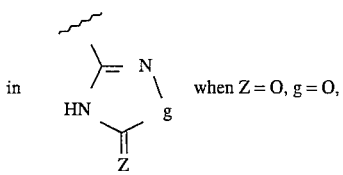 when Z = O, g = O,

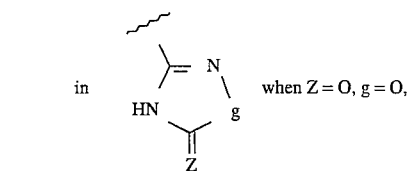

a  b  c the heterocyclic residues represented by the formula

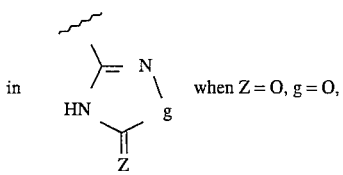

include all of the above-mentioned a, b and c.

And, the above-mentioned heterocyclic residues ($R^3$) may optionally substituted with a group represented by $R^{10}$, as shown below.

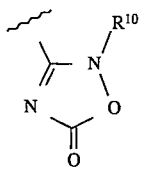    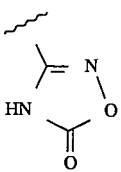

Examples of the groups represented by $R^{10}$ as mentioned above include groups represented by the formula —CH($R^4$)—OCO$R^5$ [wherein $R^4$ stands for hydrogen, a $C_{1-6}$ straight-chain or branched lower alkyl group (e.g. methyl, ethyl, n-propyl, isopropyl, n-butyl, isobutyl, t-butyl, n-pentyl, isopentyl and neopentyl), a $C_{2-6}$ straight-chain or branched lower alkenyl group or a $C_{3-8}$ cycloalkyl group (e.g. cyclopentyl, cyclohexyl and cycloheptyl); and $R^5$ stands for a $C_{1-6}$ straight-chain or branched lower alkyl group (e.g. methyl, ethyl, n-propyl, isopropyl, n-butyl, isobutyl, sec-butyl, t-butyl, n-pentyl, isopentyl and neopentyl), a $C_{2-6}$ straight-chain or branched lower alkenyl group, a $C_{3-8}$ cycloalkyl group (e.g. cyclopentyl, cyclohexyl and cycloheptyl), a $C_{1-3}$ lower alkyl group substituted with a $C_{3-8}$ cycloalkyl group (e.g. cyclopentyl, cyclohexyl and cycloheptyl) or an optionally substituted aryl group such as phenyl (e.g. benzyl, p-chlorobenzyl, phenethyl, cyclopentylmethyl and cyclohexylmethyl), a $C_{2-3}$ lower alkenyl group optionally substituted with $C_{3-8}$ cycloalkyl or an optionally substituted aryl group such as phenyl (e.g. cinnamyl, etc. having alkenyl moiety such as vinyl, propenyl, allyl, and isopropenyl), an aryl group such as optionally substituted phenyl (e.g. phenyl, p-tolyl, naphthyl), a $C_{1-6}$ straight-chain or branched lower alkoxy group (e.g. methoxy, ethoxy, n-propoxy, isopropoxy, n-butoxy, isobutoxy, sec-butoxy, t-butoxy, n-pentyloxy, isopentyloxy and neopentyloxy), a $C_{2-8}$ straight-chain or branched lower alkenyloxy group (e.g. allyloxy and isobutenyloxy), a $C_{3-8}$ cycloalkyloxy group (e.g. cyclopentyloxy, cyclohexyloxy and cycloheptyloxy), a $C_{1-3}$ lower alkoxy group substituted with $C_{3-8}$ cycloalkyl (e.g. cyclopentyl, cyclohexyl and cycloheptyl) or an aryl group such as optionally substituted phenyl (e.g. benzyloxy, phenethyloxy, cyclopentylmethyloxy and cyclohexylmethyloxy having alkoxy moiety such as methoxy, ethoxy, n-propoxy and isopropoxy), a $C_{2-3}$ lower alkenyloxy group substituted with $C_{3-8}$ cycloalkyl (e.g. cyclopentyl, cyclohexyl and cycloheptyl) or an aryl group such as optionally substituted phenyl (e.g. cinnamyloxy having alkenyloxy moiety such as vinyloxy, propenyloxy, allyloxy, isopropenyloxy) and an aryloxy group such as optionally substituted phenoxy (e.g. phenoxy, p-nitrophenoxy and naphthoxy)], an optionally substituted alkyl (e.g. a lower ($C_{1-4}$) alkyl) or acyl (e.g. a lower ($C_{2-5}$) alkanoyl, an optionally substituted benzoyl). Examples of the substituents $R^{10}$ include methyl, ethyl, propyl, t-butyl, methoxymethyl, triphenylmethyl, cyanoethyl, acetyl, propionyl, pivaloyloxymethyl, 1-(cyclohexyloxycarbonyloxy)ethyl, 5-methyl-2-oxo-1,3-dioxolen-4-ylmethyl, acetoxymethyl, propionyloxymethyl, n-butyryloxymethyl, isobutyryloxymethyl, 1-(ethoxycarbonyloxy)ethyl, 1-(acetyloxy)ethyl, 1-(isobutyryloxy)ethyl, cyclohexylcarbonyloxymethyl, benzoyloxymethyl, cinnamyl and cyclopentylcarbonyloxymethyl. As such groups as above, any one can be used, so long as they are such substituents (so-called prodrug) as being capable of readily converting, under biological or physiological conditions (e.g. in vivo reaction such as oxidation, reduction or hydrolysis catalyzed by in vivo enzymes), into a heterocyclic residue represented by the formula As tautomers of the above-mentioned heterocyclic residue (a, b and c) and the $R^{10}$-substituted heterocyclic residues (a', b'and c') are included in the heterocyclic residues as the substituent $R^3$, so the tautomers and their substituted compounds of the above-mentioned various heterocyclic residues are likewise included in the substituents $R^3$ of the present invention. And, the substituent $R^3$ may have, besides the above-mentioned groups represented by $R^{10}$, further substituents, as exemplified by an optionally substituted alkyl group (e.g. methyl and triphenylmethyl), halogen (e.g. F, Cl and Br), nitro, cyano, a lower ($C_{1-4}$) alkoxy and an optionally substituted amino group (e.g. amino, methylamino and dimethylamino).

Examples of the ring W include an optionally substituted aromatic hydrocarbon residue and a heterocyclic residue optionally containing one or two or more of N, O and S, specifically phenyl, pyridyl, pyrazinyl, pyridazinyl, thienyl, furyl, pyrrolyl, imidazolyl, pyrazolyl, isothiazolyl, isoxazolyl (preferably phenyl).

And, aromatic hydrocarbon residues and aromatic heterocyclic residues represented by the ring Y and the ring W may have substituents, as exemplified by halogen (e.g. F, Cl and Br), nitro, cyano, a lower ($C_{1-4}$) alkoxy and an optionally substituted amino group (e.g. amino, methylamino and dimethylamino).

X shows that the adjacent ring W (e.g. phenylene) and the ring Y (e.g. phenyl group) are bonded directly or through a spacer having an atomic length of two or less (preferably direct bondage), and, as the spacer having an atomic length of two or less, any one of divalent chain having one or two atomic number constituting the straight-chain portion, which may have further side chains. Specific examples of them include a lower ($C_{1-4}$) alkylene, —CO—, —O—, —S—, —NH—, —CO—NH—, —O—CH$_2$—, —S—CH$_2$— and —CH=CH—.

The symbol n denotes an integer of 1 or 2 (preferably 1).

Among the groups represented by the formula

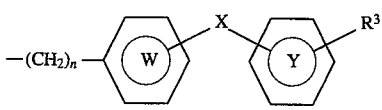

consisting of $R^3$, W, X, Y and n, those represented by the formula

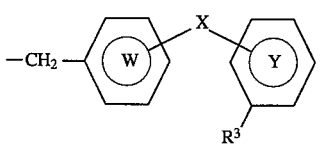

for example,

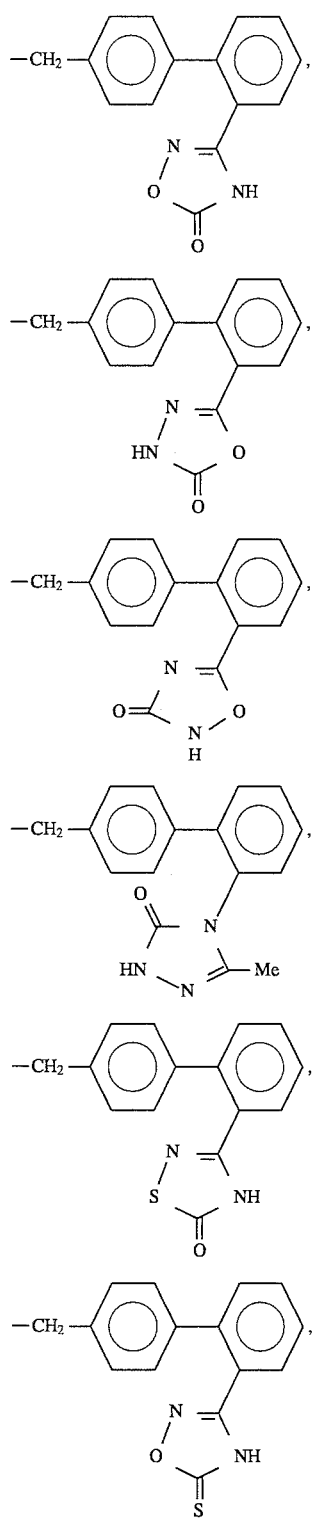

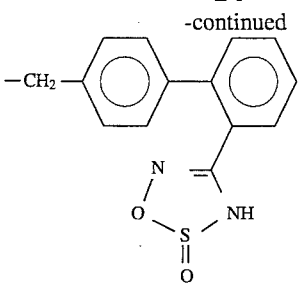

are preferable.

Among the compounds represented by the above-mentioned formula ( I ), those represented by the formula

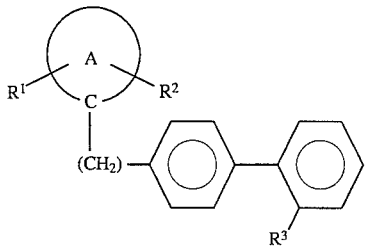
(I')

[wherein aromatic heterocyclic groups represented by the ring A are exemplified by,

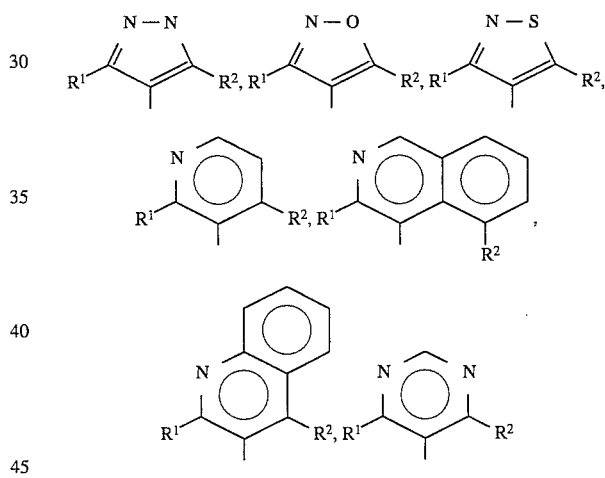

$R^1$ may be bonded through a hetero atom (e.g. O, N(H) and S) and stands for an optionally substituted lower ($C_{1-6}$) alkyl (preferably a lower ($C_{2-4}$) alkyl); $R^2$ stands for a group represented by the formula —CO—D" [wherein D" stands for hydroxyl group, amino, N-lower ($C_{1-4}$) alkylamino, N,N-di-lower ($C_{1-4}$) alkylamino or a lower ($C_{1-4}$) alkoxy whose alkyl moiety is optionally substituted with hydroxyl group, amino, halogen, a lower ($C_{2-6}$) alkanoyloxy (e.g. acetyloxy and pivaloyloxy), lower ($C_{3-7}$) cycloalkanoyloxy, 1-lower ($C_{1-6}$) alkoxycarbonyloxy (e.g. methoxycarbonyloxy, ethoxycarbonyloxy), lower ($C_{3-7}$) cycloalkoxycarbonyloxy (e.g. cyclohexyloxycarbonyloxy) or a lower ($C_{1-4}$) alkoxy; $R^3$ stands for groups represented by the formula,

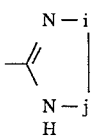

wherein i stands for —O— or —S—; j stands for >=O, >=S or >S(O)$_m$; and m is of the same meaning as defined above, which are optionally protected with optionally substituted lower (C$_{1-4}$) alkyl (e.g. methyl, triphenylmethyl, methoxymethyl, acetyloxymethyl, methoxycarbonyloxymethyl, ethoxycarbonyloxymethyl, 1-(cyclohexyloxycarbonyloxy)ethyl and pivaloyloxymethyl) or an acyl group (e.g. a lower (C$_{2-5}$) alkanoyl and benzoyl).

Incidentally, the compounds of the above-mentioned formula (I') wherein R$^2$ stands for N-hydroxycarbamimidoyl (—C(=N—OH)—NH$_2$) are useful as intermediates for synthesizing compounds (I') wherein R$^2$ stands for oxadiazole or thiadiazole ring residue.

Production Method

The compound represented by the above-mentioned formula (I) can be produced by, for example, methods as shown below.

Reaction (a)

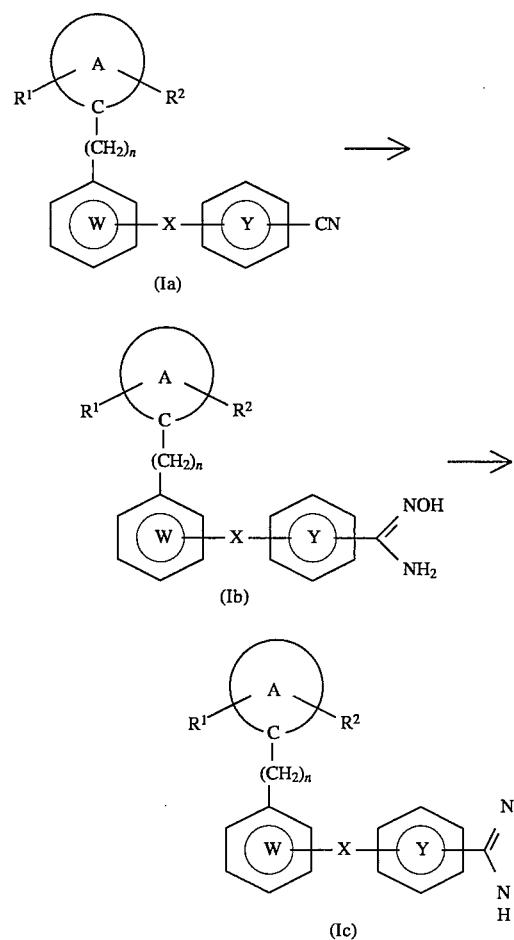

[wherein A, R$^1$ R$^2$, W, X, Y and n are of the same meaning as defined above].

The reaction (a) is to obtain the oxadiazolone compound (Ic) by leading the cyano compound (Ia) to the amidoxime compound (Ib), which is then subjected to ring-closing reaction.

The reaction of obtaining the compound (Ib) is conducted in a conventional organic solvent, using about 2–10 moles of hydroxylamine relative to one mole of the compound (Ia).

Examples of the solvent include amides (e.g. dimethylformamide and dimethylacetamide), sulfoxide (e.g. dimethyl sulfoxide), alcohols (e.g. methanol and ethanol), ethers (e.g. dioxane and tetrahydrofuran) and halogenated hydrocarbons (e.g. methylene chloride and chloroform).

The reaction using hydroxylamine is conducted, when an inorganic acid salt (e.g. hydroxylamine hydrochloride or hydroxylamine sulfate) or an organic acid salt (e.g. hydroxylamine oxalate), in the coexistence of equimolar amount of a suitable base (e.g. potassium carbonate, sodium carbonate, sodium hydroxide, triethylamine, sodium methanolate, sodium ethanolate and sodium hydride). While the reaction conditions vary with the reagent or the solvent then employed, it is preferable to allow the reaction to proceed for about 2 to 24 hours at temperatures ranging from about 50° to 100° C., after processing hydroxylamine hydrochloride with sodium methoxide or trimethylamine in dimethyl sulfoxide.

The amidoxime compound (Ib) thus obtained is allowed to react with chloroformate (e.g. methyl ester and ethyl ester) in a conventional organic solvent (e.g. chloroform, methylene chloride, dioxane, tetrahydrofuran, acetonitrile and pyridine) in the presence of a base (e.g. triethylamine, pyridine, potassium carbonate and sodium carbonate) to afford the o-acyl compound.

While the reaction conditions vary with the reagent or the solvent then employed, the reaction is conducted preferably at temperatures ranging from 0° C. to room temperature for about 1 to 5 hours in the presence of usually 2 to 5 moles of ethyl chloroformate and about 2 to 5 moles of triethylamine relative to 1 mole of amidoxime compound (Ib).

In the reaction of obtaining the ring-closed compound (Ic) from o-acyl amidoxime thus obtained, the object compound can be readily obtained by heating in a conventional organic solvent.

As the solvent, use is made of aromatic hydrocarbons (e.g. benzene, toluene and xylene), ethers (e.g. dioxane and tetrahydrofuran) or halogenated hydrocarbons (e.g. dichloroethane and chloroform). The reaction is conducted preferably by heating the o-acyl amidoxime compound in xylene under reflux for about 1 to 3 hours.

Reaction (b)

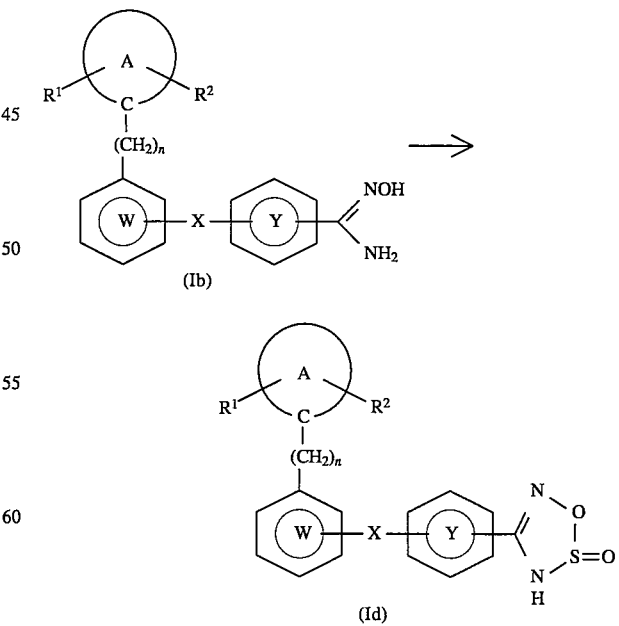

[wherein A, R$^1$ R$^2$, W, X, Y and n are of the same meaning as defined above].

The above-mentioned reaction (b) is to obtain the oxathiadiazole derivative (Id) by subjecting the amidoxime compound (Ib) obtained by Reaction (a) to ring-closure.

The amidoxime compound (Ib) is allowed to react with thionyl chloride in a conventional organic solvent (e.g. dichloromethane, chloroform, dioxane and tetrahydrofuran) in the presence of a base (e.g. pyridine and triethylamine) to give the compound (Id).

While the reaction conditions vary with the reagent or the solvent then employed, the reaction is conducted by adding about 2 to 10 moles of thionyl chloride in the presence of about 1 to 3 moles of pyridine relative to one mole of the amidoxime compound (Ib) by using dichloromethane as the solvent while cooling at temperatures ranging from 0° to −30° C., and the reaction is preferably allowed to proceed for a period ranging from 30 minutes to one hour.

Reaction (c)

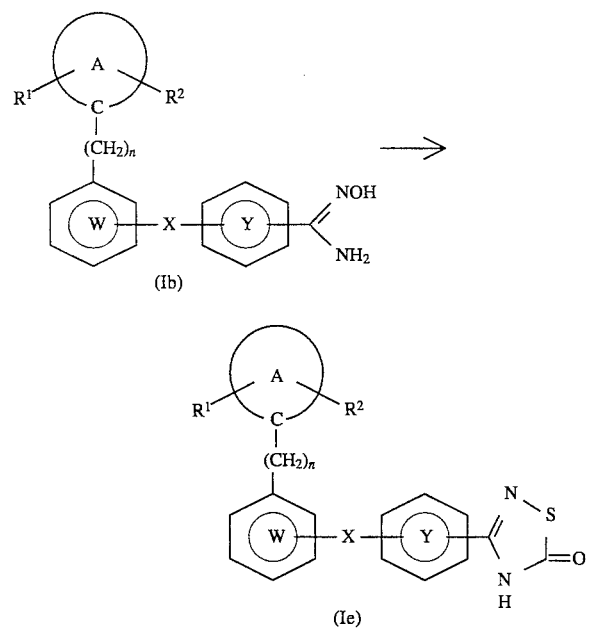

[wherein A, $R^1$, $R^2$, W, X, Y and n are of the same meaning as defined above].

The above-mentioned reaction (c) is to obtain the thiadiazolone compound (Ie) by subjecting the amidoxime compound (Ib) obtained in the above-mentioned reaction (a) to ring closure.

The reaction of obtaining the compound (Ie) is conducted by using about 1 to 2 moles of 1,1'-thiocarbonyl diimidazole relative to one mole of the compound (Ib) in a conventional organic solvent in the presence of 1 to 10 equivalents of a Lewis acid (e.g. boron trifluoride diethyl ether complex, stannous chloride, stannic chloride, zinc chloride, cuprous chloride and silica gel).

As the solvent, use is made of, for example, ethers (e.g. dioxane and tetrahydrofuran) and halogenated hydrocarbons (e.g. methylene chloride and chloroform).

Alternatively, the compound (Ib) is dissolved in a mixture of methanol and chloroform, to which is added 1,1'-thiocarbonyl diimidazole while stirring, together with silica gel, at temperatures ranging from 0° C. to room temperature, then the reaction is allowed to proceed, preferably, at about room temperature for about 30 minutes to two hours.

Reaction (d)

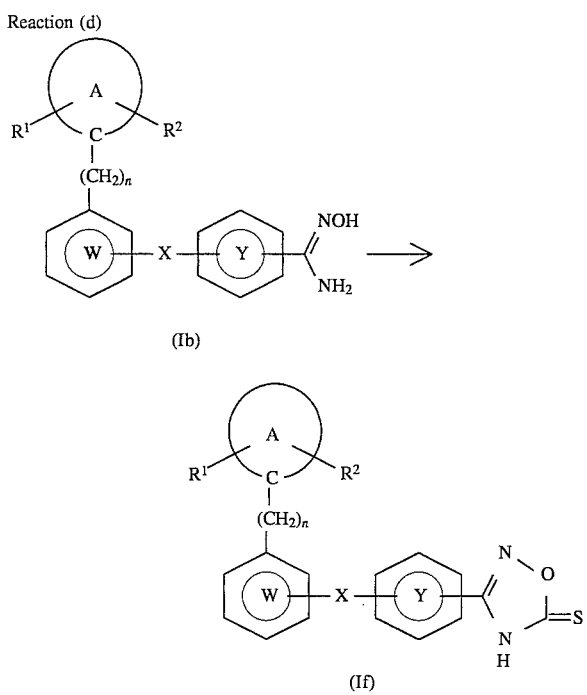

[wherein A, $R^1$, $R^2$, W, X, Y and n are of the same meaning as defined above]

The above-mentioned reaction (d) is to obtain the thioketone compound (If) by subjecting the amidoxime compound (Ib) obtained in the above-mentioned reaction (a) to ring closure.

The reaction of obtaining the compound (If) is conducted by using about 1 to 10 moles of 1,1'-thiocarbonyl diimidazole relative to 1 mole of the compound (Ib) in a conventional solvent in the presence of a base.

Examples of the solvent include ethers (e.g. dioxane and tetrahydrofuran), halogenated hydrocarbons (e.g. methylene chloride and chloroform), acetonitrile and acetone.

And, examples of the base include amines (e.g. triethylamine, pyridine, 2,6-dimethyl pyridine, 1,5-diazabicyclo [4.3.0]non-5-ene and 1,8-diazabicyclo [5.4.0]-7-undecene), or the like.

While the reaction conditions vary with the reagent or the solvent then employed, the reaction is preferably conducted by dissolving the compound (Ib) in acetonitrile at temperatures ranging from about 0° C. to room temperature for about 10 minutes to 24 hours.

And, the above-mentioned reaction (d) can also be conducted under such reaction conditions as described below.

The reaction is conducted by using about 1 to 10 moles of acetic anhydride relative to 1 mole of the compound (Ib) in a conventional solvent in the presence of a base.

As the solvent, use is made of halogenated hydrocarbons (e.g. methylene chloride and chloroform), ethers (e.g. dioxane and tetrahydrofuran) or the like.

And, as the base, mention is made of amines (e.g. trimethylamine and pyridine). The reaction is preferably conducted by dissolving the compound (Ib) in methylene chloride at temperatures ranging form 0° C. to room temperature for about 1 to 5 hours.

One mole of thus-obtained O-acetyl amidoxime is allowed to react with about 3 to 10 moles of carbon disulfide in an organic solvent in the presence of a base to thereby obtain the thioketone compound (If).

As the solvent, use is made of amides (e.g. N,N-dimethylformamide and dimethylacetamide) or dimethyl sulfoxide or the like.

As the base, mention is made of sodium hydride, potassium t-butoxide or the like.

The reaction is preferably conducted by adding sodium hydride in limited amounts, while stirring O-acetyl amidoxime and carbon disulfide in dimethylformamide at room temperature, and the reaction is allowed to proceed for about 1 to 3 hours.

Reaction (e)

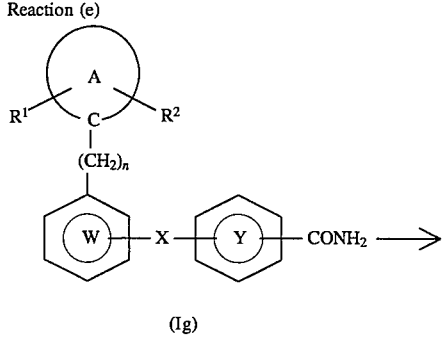

(Ig)

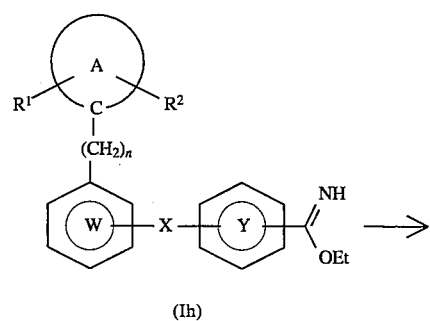

(Ih)

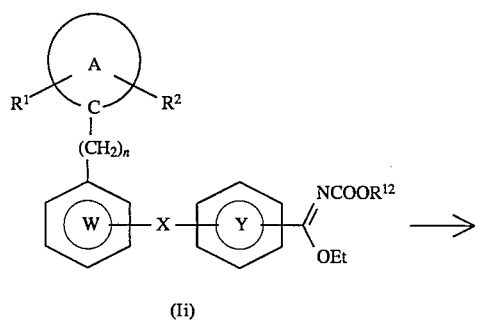

(Ii)

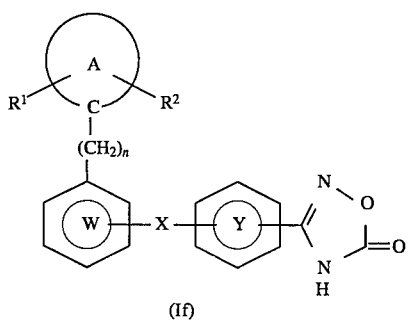

(If)

[wherein A, $R^1$, $R^2$, W, X, Y and n are of the same meaning as defined above, and $R^{12}$ stands for a lower ($C_{1-8}$) alkyl group.]

In the above-mentioned formula (e), the imino ether compound (Ih) can be obtained in a good yield by allowing the amide compound (Ig) to react with about 1 to 2 times as much moles of triethyloxonium tetrafluoroborate in a halogenated hydrocarbon (e.g. methylene chloride or chloroform) at temperatures ranging from 0° C. to room temperature for about 30 minutes to 2 hours.

Then, the iminoether compound (Ih) is allowed to react with 1 to 2 times as much moles of chloroformate (e.g. methyl chloroformate or ethyl chloroformate) in a conventional organic solvent (e.g. benzene, toluene, methylene chloride, chloroform, dioxane or pyridine) in the presence of 1 to 2 times as much moles of a base (e.g. 2,4,6-trimethylpyridine, triethylamine, dimethylpyridine, methylpyridine or diethylaniline). While the reaction conditions vary with the reagent or the solvent then employed, the reaction is allowed to proceed in toluene at temperatures ranging from about 80° to 100° C for about 1 to 3 hours to thereby afford the N-alkoxycarbonyl compound (Ii) in a good yield. The N-alkoxycarbonyl compound (Ii) thus obtained is allowed to react with about two times as much moles of hydroxylamine hydrochloride and base (e.g. sodium methoxide, sodium ethoxide or potassium carbonate) in alcohol (e.g. methanol or ethanol) to cause ring closure reaction. The reaction is allowed to proceed preferably at temperatures ranging from 50° C. to about the boiling point of the solvent for about 3 to 10 hours.

Reaction (f)

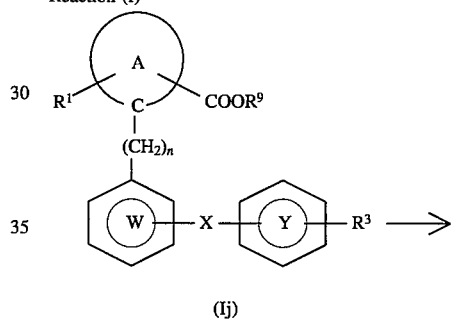

(Ij)

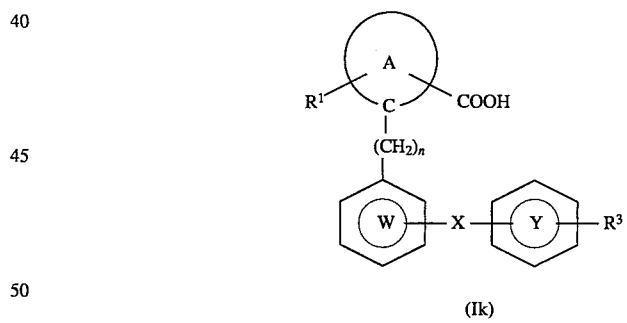

(Ik)

[wherein A, $R^1$, $R^2$, $R^9$, W, X, Y and n are of the same meaning as defined above]

The above-mentioned reaction (f) is to obtain carboxylic acid (Ik) by subjecting the ester compound (Ij) to alkali hydrolysis.

The hydrolysis is conducted by using about 1 to 3 moles of alkali relative to 1 mole of the compound (Ij) in a solvent, usually an aqueous alcohol (e.g. methanol, ethanol or methyl cellosolve).

As the alkali, use is made of lithium hydroxide, sodium hydroxide, potassium hydroxide or the like.

The reaction is allowed to proceed at temperatures ranging from room temperature to about 100° C. for about 1 to 10 hours, preferably at about the boiling point of the solvent for about 3 to 5 hours.

Reaction (g)

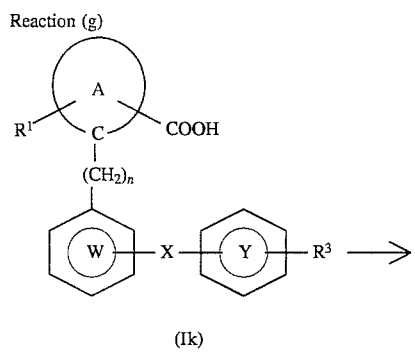

(Ik)

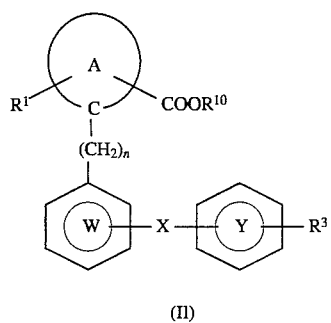

(II)

[wherein A, R¹, R³, R¹⁰, W, X, Y and n are of the same meaning as defined above]

The above-mentioned reaction (g) is alkylation using an alkylating agent in the presence of a base.

The alkylation is conducted, employing 1 to 3 moles of a base and approximately 1 to 3 moles of the alkylating agent usually in a solvent such as dimethylformamide, dimethylacetamide, dimethyl sulfoxide, acetonitrile or ethyl methyl ketone.

Examples of the base include sodium hydroxide, potassium t-butoxide, potassium carbonate, sodium carbonate or the like.

As the alkylating agent, use is made of substituted halogenide (e.g. chloride, bromide and iodide), substituted sulfonic acid esters (e.g. p-toluenesulfonate).

While the reaction conditions vary with the combination of the base and the alkylating agent then employed, it is preferable to conduct the reaction usually at temperatures ranging from 0° C. to about room temperature for about 1 to 10 hours.

And, when chloride or bromide is employed as the alkylating agent, it is preferable to conduct the reaction by adding potassium iodide or sodium iodide to accelerate the reaction.

Reaction (h)

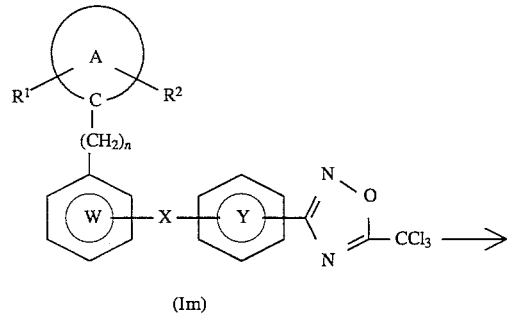

(Im)

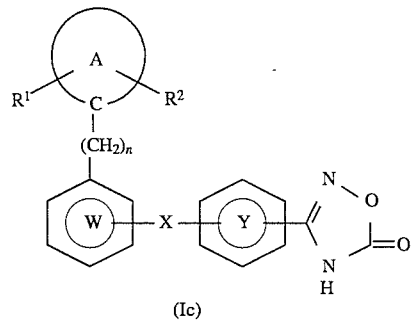

(Ic)

[wherein A, R¹, R², W, X, Y and n are of the same meaning as defined above]

The above-mentioned reaction (h) is to obtain the oxadiazolone (Ic) by subjecting the trichloromethyl oxadiazole compound (Im) to hydrolysis using an alkali in an organic solvent of aqueous organic solvent.

Examples of the organic solvents include ethers (e.g. dioxane and tetrahydrofuran) and alcohols (e.g. methanol and ethanol).

As the alkali, mention is made of sodium hydroxide, potassium hydroxide and lithium hydroxide.

Preferably, the compound (VI) is allowed to react in dioxane at temperatures ranging from 0° C. to about room temperature for about 30 minutes to 2 hours with about 2 to 10 moles of a 0.5 to 1N aqueous solution of sodium hydroxide.

The reaction products obtained as above by the reactions (a) to (h) can easily be isolated by conventional isolation and purification processes, for example, column chromatography and recrystallization.

Incidentally, these compounds (I) can be led, by conventional methods, to salts with physiologically acceptable acids or bases. These salts include, for example, salts with an inorganic acid such as hydrochloric acid, sulfuric acid and nitric acid and, depending on the compounds, salts with an organic acid such as acetic acid, oxalic acid, succinic acid and maleic acid, salts with an alkali metal such as sodium and potassium, and salts with an alkaline earth metal such as calcium.

The starting compounds can be synthesized by, for example, the methods described as follows.

Reaction (i)

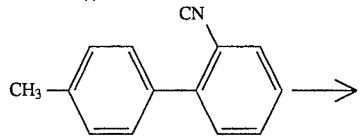

(IIa)

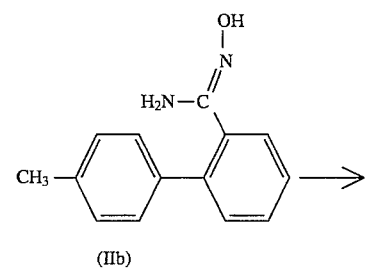

(IIb)

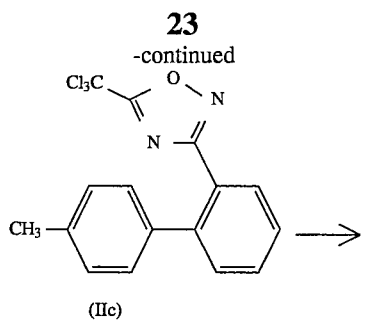

(IIc)

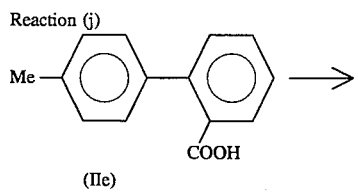

(IId)

[wherein L stands for halogen atom or substituted sulfonic acid ester]

The above-mentioned reaction (i) is to obtain the compound (IId), by leading the cyano compound (IIa) to the amidoxime compound (IIb) under substantially the same reaction conditions as in the above-mentioned reaction (a), then subjecting the amidoxime derivative(s) (IIb) to cyclization to give the oxadiazole derivative(s) (IIc), followed by subjecting the oxadiazole derivative(s) (IIc) to halogenation.

The amidoxime compound (IIb) obtained from the compound (IIa) by substantially the same procedure as in reaction (a) is allowed to react with about 1 to 10 moles of trichloroacetic acid anhydride or hexachloroacetone relative to one mole of the amidoxime (IIb) in accordance with the method described in the literature reference [F. Eloy, et al., Helv. Chim. Acta, 49, 1430(1966)] to give the oxadiazole derivatives (IIc), then the compound (IIc) thus obtained is allowed to react with about 1 to 1.5 mole of a halogenating agent (e.g. N-bromosuccinimide and N-bromoacetamide) relative to 1 mole of the compound (IIc) in halogenated hydrocarbon (e.g. carbon tetrachloride) at temperatures ranging from 50° C. to the boiling point of the solvent then employed for about 1 to 3 hours, in the presence of a catalytic amount of an initiator (e.g. benzoyl peroxide and azobisisobutyronitrile). This reaction can also be carried out under irradiation of light.

Reaction (j)

(IIe)

(IIf)

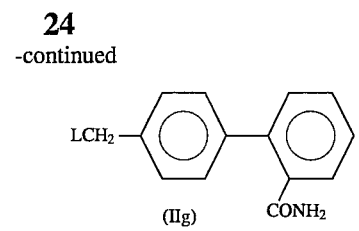

(IIg)

[wherein L is of the same meaning as defined above]

The reaction (j) comprises converting carboxylic acid (IIe) to amide (IIf) in accordance with a conventional manner, then leading (IIf) to the halogenide (IIg).

The carboxylic acid (IIe) is allowed to react with about 2 to 5 moles of a halogenating agent (e.g. oxalyl chloride or thionyl chloride) in an organic solvent (e.g. tetrahydrofuran, chloroform or methylene chloride) at temperatures ranging from room temperature to the boiling point of the solvent then employed for about 1 to 20 hours. It is preferable to accelerate this reaction by the addition of a catalytic amount of dimethylformamide. The acid halogenide thus obtained is preferably allowed to react with an excess volume of of aqueous ammonia in an organic solvent (e.g. tetrahydrofuran or dioxane) at temperatures ranging from 0° C. to room temperature for about 1 to 10 hours, so that the amide derivative (IIf) can be obtained in a good yield. The reaction to obtain the halogenide (IIg) from the amide derivative (IIf) thus obtained is conducted preferably in substantially the same manner as described in the reaction (i).

Reaction (k)

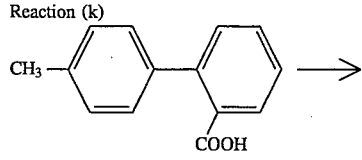

(IIe)

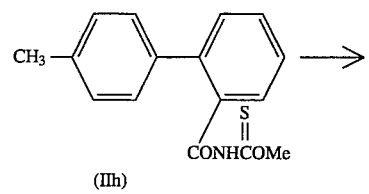

(IIh)

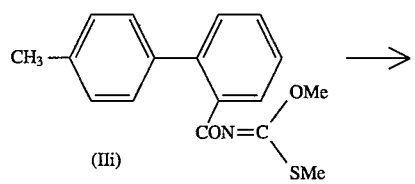

(IIi)

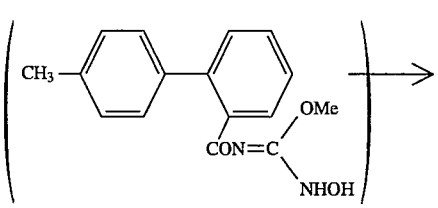

-continued

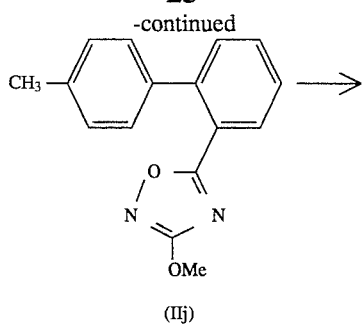

(IIj)

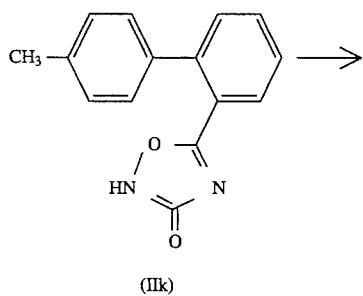

(IIk)

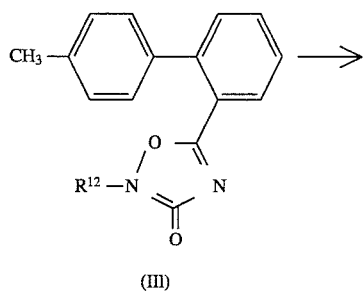

(Ill)

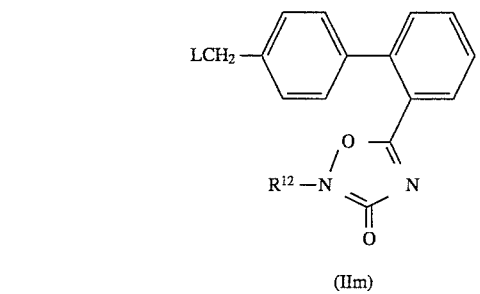

(IIm)

[wherein $R^{13}$ stands for an optionally substituted alkyl group shown by the above-mentioned $R^{10}$ (e.g. triphenyl-methyl, methoxymethyl and cyanoethyl) or t-butyldimethylsilyl group; and L is of the same meaning as defined above]. The reaction (k) is to obtain the oxadiazole derivative (IIj), which comprises leading carboxylic acid (IIe) to acyl isothiocyanate by a conventional method, allowing the latter to react with alcohol to give carbonyl thiocarbamate (IIh), subjecting the compound (IIh) to methylation to give carbonate (IIi), then allowing the compound (IIi) to react with hydroxylamine, followed by cyclization under heating.

In the reaction for obtaining carbonyl thiocarbamate (IIh) from carboxylic acid (IIe), the compound (IIe) is allowed to react with about 2 to 5 moles of a halogenating agent (e.g. thionyl chloride) relative to one mole of (IIe) in halogenated hydrocarbon (e.g. chloroform and methylene chloride) for about 1 to 5 hours at temperatures ranging from 50° C. to the boiling point of the solvent then employed to give acid chloride. The acid chloride thus obtained is allowed to react with about 2 to 5 moles of thiocyanate (e.g. sodium salt and potassium salt) in ether (e.g. dioxane and tetrahydrofuran) at temperatures ranging from 50° C. to the boiling point of the solvent then employed for about 1 to 3 hours to give isothiocyanate. It is preferable to subject the isothiocyanate thus obtained to heating together with about 2 to 10 moles of alcohol (e.g. methanol and ethanol) at temperatures ranging from about 50° C. to the boiling point of the solvent then employed for about 15 minutes to one hour.

In the reaction for obtaining iminomonothiocarbonate (IIi) from the compound (IIh), it is preferable to allow the compound (IIh) to react with methyl iodide (molar ratio=1: about 1 to 2) in an organic solvent (e.g. methanol, ethanol, dimethylformamide (DMF) and acetonitrile), in the presence of about 1 to 2 moles, relative to one mole of (IIh), of a base (e.g. NaOMe, $Na_2CO_3$ and $K_2CO_3$) at temperatures ranging from room temperature to about 50° C. for about 10 to 24 hours.

In the reaction for obtaining oxadiazole derivative (IIj) from the compound (IIi), it is preferable to allow (IIi) to react with hydroxylamine (molar ratio=1: about 1 to 2) in alcohol (e.g. methanol and ethanol) at temperatures ranging from room temperature to about 50° C. for about 10 to 20 hours, followed by subjecting the reaction mixture to heating in an organic solvent (e.g. toluene and benzene) in the presence of a catalytic amount of an acid (e.g. p-toluenesulfonic acid) at temperatures ranging from about 50° C. to the boiling point of the solvent then employed for about 1 to 3 hours.

In the reaction for obtaining the demthylated compound (IIk) from the compound (IIj), it is preferable to subject an excess amount of pyridine hydrochloride and (IIj) to fusing reaction in nitrogen streams at temperatures ranging from about 150° to 160° C for about 0.5 to 1 hour.

In the reaction for obtaining the compound (Ill) from the compound (IIk), it is preferable to allow the compound (IIk) to react with an alkylating agent (e.g. triphenylmethyl chloride, methoxymethyl chloride and cyanoethyl chloride) (molar ratio=1: about 1 to 2) in an organic solvent (e.g. chloroform, methylene chloride, dioxane, tetrahydrofuran and pyridine) in the presence of about 1 to 2 moles of a base (e.g. potassium carbonate, sodium carbonate, triethylamine and pyridine) at temperatures ranging from 0° C. to about room temperature for about 1 to 3 hours.

The reaction for obtaining the compound (IIm) by halogenating the compound (Ill) can be conducted in substantially the same manner as in the reaction for obtaining the compound (IId) from the compound (IIc) in the above-mentioned reaction (i).

Reaction (l)

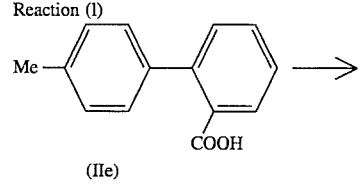

(IIe)

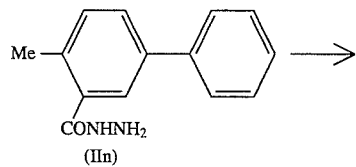

(IIn)

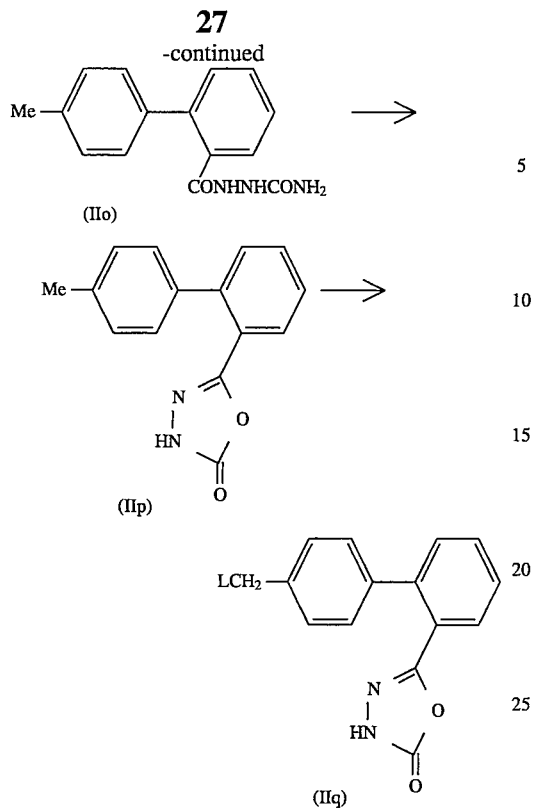

(IIo)

(IIp)

(IIq)

[wherein L is of the same meaning as defined above].

The reaction (1) comprises converting the carboxylic acid (IIe) to semicarbazide (IIo) via hydrazide (IIn) in accordance with a conventional manner, then subjecting (IIo) to dehydrocyclization to give oxadiazolone (IIp), followed by leading (IIp) to the halogeno compound (IIq).

In the reaction for obtaining hydrazide (IIn) from carboxylic acid (IIe), (IIe) is allowed to react with about 2 to 5 moles of a halogenating agent (e.g. oxalyl chloride and thionyl chloride) in an organic solvent (e.g. tetrahydrofuran, chloroform and methylene chloride) at temperatures ranging from room temperature to the boiling point of the solvent then employed for about 1 to 20 hours. In this case, it is preferable to add a catalytic amount of dimethylformamide to accelerate the reaction. The acid chloride thus obtained is allowed to react with about 2 to 5 moles of hydrazine hydrate in an organic solvent (e.g. tetrahydrofuran and dioxane) at temperatures ranging from room temperature to about 50° C. for about 1 to 10 hours to obtain the compound (IIn).

In the reaction for producing semicarbazide (IIo) from the hydrazide (IIn) thus obtained, it is preferable to allow (IIn) to react with about 2 to 5 moles of isocyanate (e.g. sodium or potassium salt) in an aqueous solution in the presence of an acid (e.g. hydrochloric acid or sulfuric acid) in an amount equal to that of the isocyanate then employed at temperatures ranging from 0° C. to room temperature for about 1 to 5 hours.

In the reaction for producing oxadiazolone (IIp) from the semicarbazide (IIo) thus obtained, it is preferable to heat (IIo) in an organic solvent (e.g. benzene and xylene) at about the boiling point of the solvent then employed for about 5 to 20 hours.

The reaction for producing the halogeno-compound (IIq) from the oxadiazolone (IIp) thus obtained is preferably conducted in a manner similar to that described in the above-mentioned reaction (i).

Reaction (m)

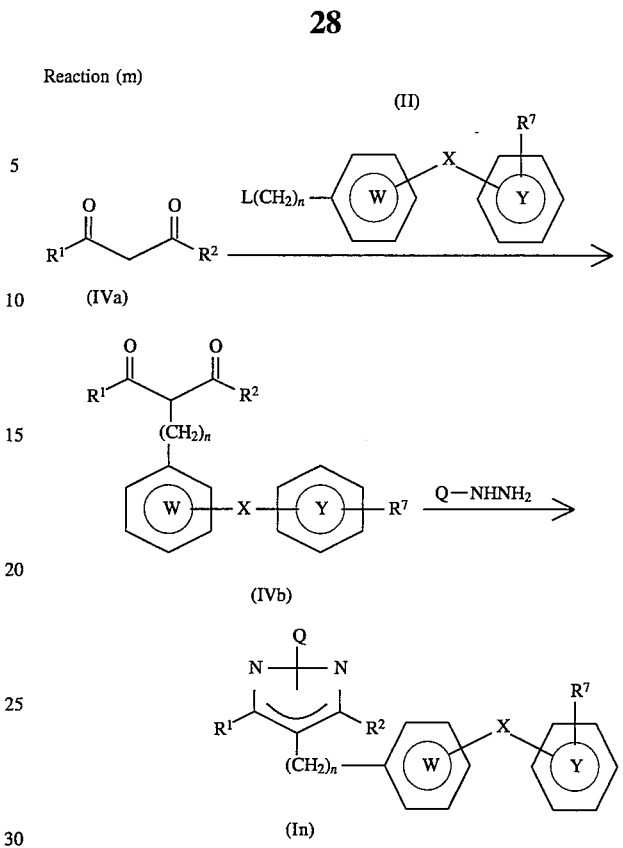

[wherein $R^1$, $R^2$, W, X, Y, Q and n are of the same meaning as defined above, and $R^7$ stands for a substituent shown by the afore-mentioned $R^3$ or cyano group, carboxyl group, carbamoyl group, a lower ($C_{1-4}$) alkylcarbamoyl group, a lower ($C_{1-6}$) alkoxycarbonyl group, nitro group, formyl group, hydroxymethyl group and a lower ($C_{1-4}$) alkyl group.]

The above reaction (m) is alkylation by allowing an alkylating agent (II) to act on the diketone compound (IVa) in the presence of a base.

The alkylation is conducted by using 1 to 3 moles of the base and about 1 to 3 moles of the alkylating agent relative to one mole of the compound (IVa) usually in a solvent such as dimethylformamide, dimethylacetamide, dimethyl sulfoxide, acetonitrile, acetone, ethyl methyl ketone, tetrahydrofuran and dioxane, or hydrocarbon such as toluene and benzene. Using, as the base, sodium hydride, potassium t-butoxide, potassium carbonate, sodium carbonate or sodium methoxide, the alkylation is conducted at temperatures ranging from 0° to about 150° C. for about 1 to 50 hours to give the alkylated product (IVb) in a good yield.

Then, the compound (IVb) is allowed to react with 1 to 10 times as much moles of substituted or unsubstituted hydrazine in a conventional solvent (e.g. aqueous alcohol, ethanol, ether, tetrahydrofuran, dioxane, dimethylformamide, dimethylacetamide, dimethyl sulfoxide, 2-methoxyethanol and acetic acid) at temperatures ranging from 0° to about 100° C. for about 1 to 60 hours to thereby obtain pyrazole (In) in a good yield.

Reaction (n)

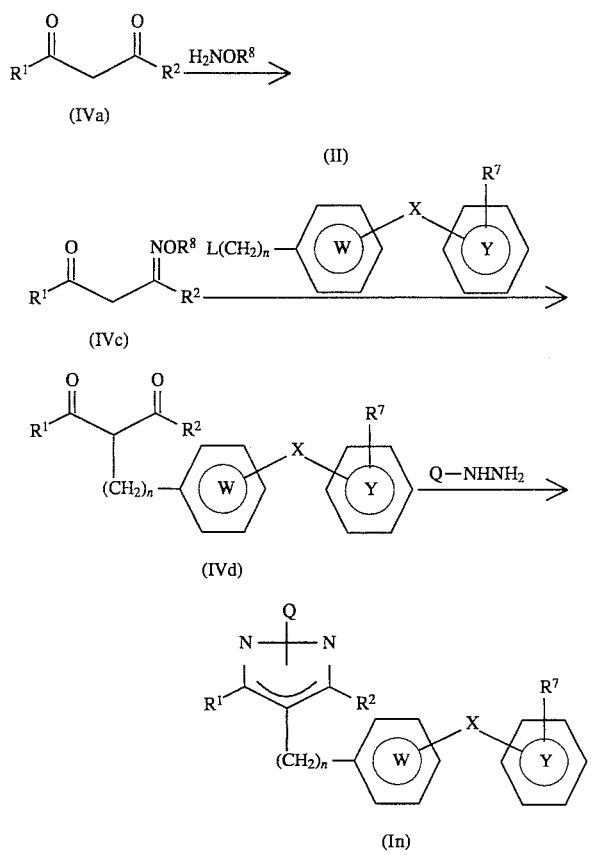

[wherein $R^1$, $R^2$, $R^7$, W, X, Y, Z and n are of the same meaning as defined above, and $R^8$ stands for a lower ($C_{1-4}$) alkyl group or benzyl group.]

In the above-mentioned formula (n), the diketone compound (IVa) is allowed to react with 1 to 20 times as much moles of o-alkyl or benzyl hydroxylamine usually in a solvent such as alcohol, tetrahydrofuran, dioxane, dimethylformamide, dimethyl sulfoxide and 2-methoxyethanol at temperatures ranging from 0° to about 100° C. for about 1 to 24 hours to thereby obtain the imide (IVc) in a good yield.

The subsequent reaction for obtaining the alkylated compound (IVd) by allowing the alkylating agent (II) to act on the imide compound (IVc) is preferably conducted in substantially the same manner as described in the reaction (m).

Further reaction for obtaining pyrazole (In) from the alkylated compound (IVd) is preferably conducted in substantially the same manner as described in the reaction (m).

Reaction (o)

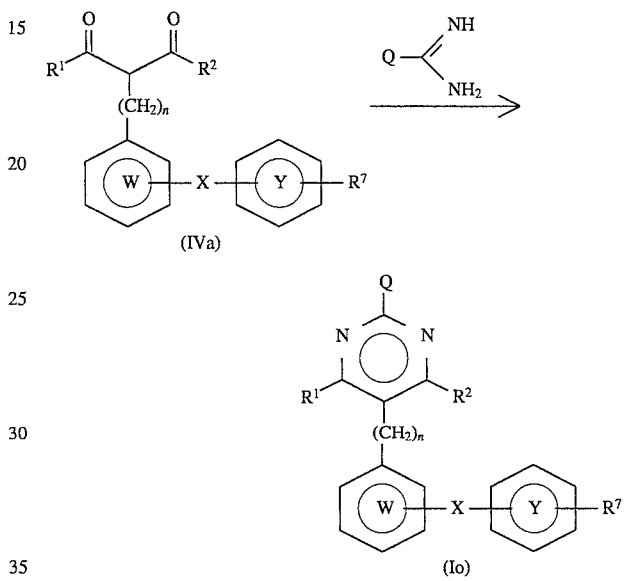

[wherein $R^1$, $R^2$, $R^7$, W, X, Y, Q and n are of the same meaning as defined above.]

The above-mentioned reaction (o) is to obtain the pyrimidine (Io) by subjecting the diketone compound (IVa) to dehydrocyclization with amidine, guanidine, o-alkyl or aryl isourea, s-alkyl or aryl isothiourea.

Reaction (p)

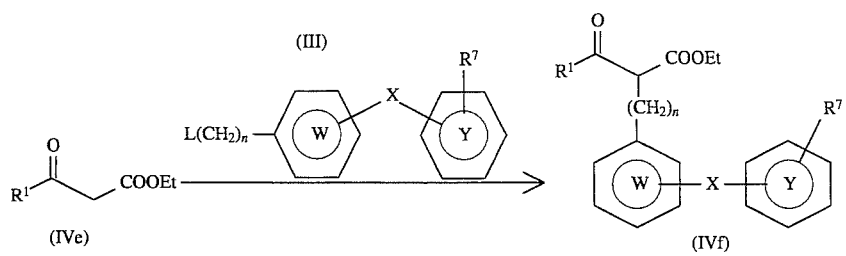

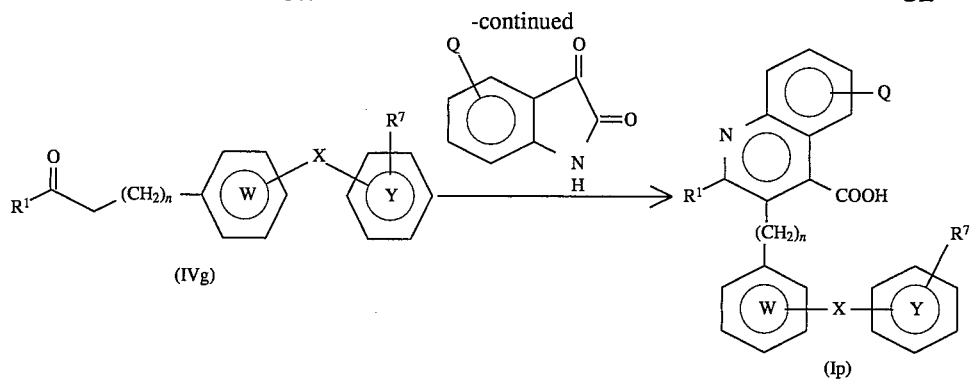

(IVg) → (Ip)

[wherein $R^1$, $R^7$, L, W, X, Y, Q and n are of the same meaning as defined above.]

In the above reaction (p), the keto ester (IVe) is alkylated with the alkylating agent (II) in the same manner as shown in the reaction (m) to give the compound (IVf), which is subjected to hydrolysis and decarboxylation to afford the ketone compound (IVg). Then, the ketone compound (IVg) is allowed to react with isatin in a solvent (e.g. alcohol, 2-methoxyethanol. dioxane and water) in the presence of a base such as sodium hydroxide or potassium hydroxide for 5 to 10 days at 50° to 150° C. to thereby obtain quinoline (Ip).

Reaction (q)

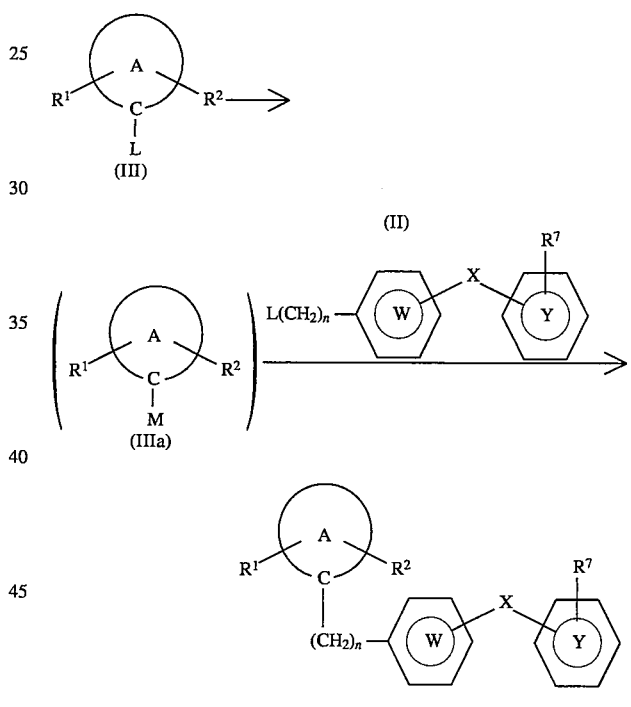

[wherein $R^1$, $R^2$, $R^7$, L, W, X, Y and n are of the same meaning as defined above; M stands for a metal (e.g. lithium, magnesium, activated zinc and cadmium).]

In the above reaction (q), the compound (II) is allowed to react with 1 to 3 times as much moles of a metal to give the organometallic compound (IIr), which is then allowed to react with the aromatic heterocyclic compound (III) usually in an organic solvent such as ether (tetrahydrofuran, diethyl ether and dioxane) or toluene for about 1 to 24 hours at temperatures ranging from about −100° to 100° C. in the presence of a catalyst (tetrakis(triphenylphosphine)palladium, palladium acetate, bis(triphenylphosphine)nickel chloride or the like) to afford the alkylated compound (In).

Reaction (r)

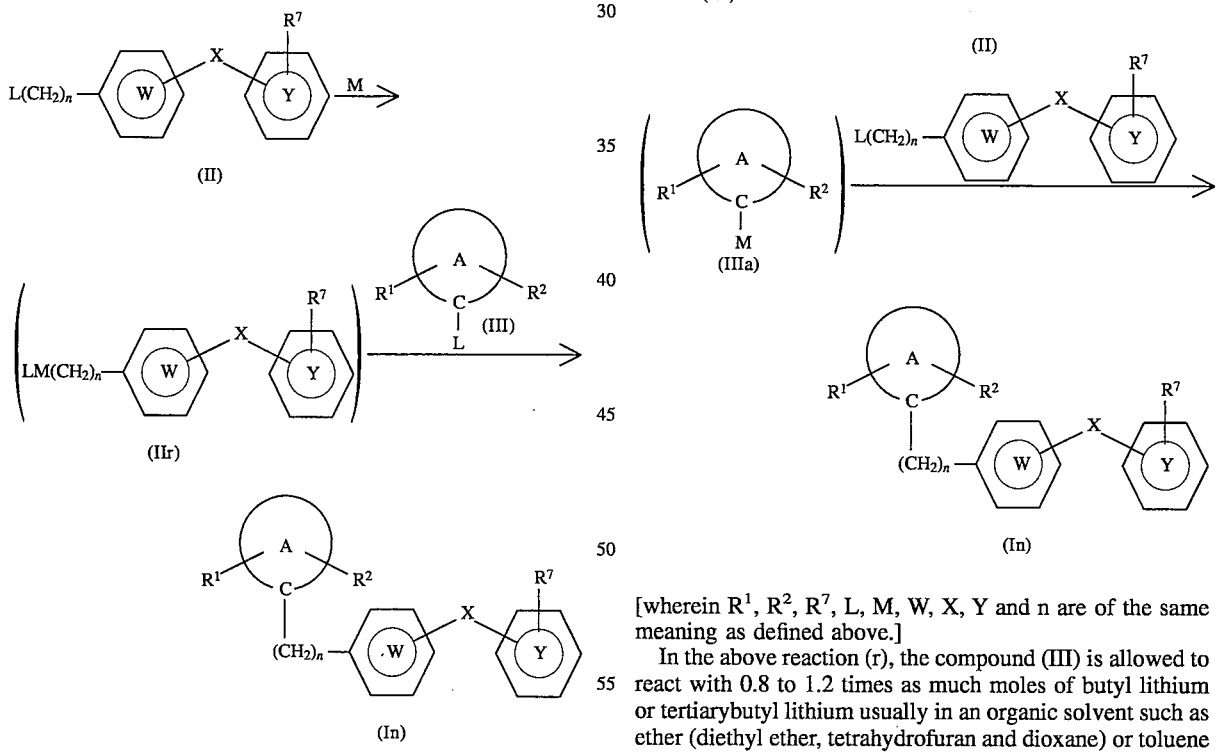

[wherein $R^1$, $R^2$, $R^7$, L, M, W, X, Y and n are of the same meaning as defined above.]

In the above reaction (r), the compound (III) is allowed to react with 0.8 to 1.2 times as much moles of butyl lithium or tertiarybutyl lithium usually in an organic solvent such as ether (diethyl ether, tetrahydrofuran and dioxane) or toluene at temperatures ranging from about −100° to 50° C. for about 10 minutes to 3 hours to give the organometallic compound (IIIa), which is allowed to react with the alkylating agent (II) in the same solvent at temperatures ranging from −100° to 50° C. for a period ranging from 10 minutes to 24 hours to thereby obtain the alkylated compound (In).

The compounds (I) and their salts thus produced are relatively less toxic, strongly inhibit the vasoconstrictive and hypertensive actions due to angiotensin II, exert a hypotensive effect in animals, especially mammals (e.g. human being, dog, rabbit and rat), and therefore they are useful as a therapeutic agent for not only hypertension but also circulatory diseases such as cardiac diseases (hypertrophy of the heart, cardiac insufficiency, cardiac infarction or the like), cerebral apoplexy, nephropathy and arteriosclerosis. And, the compound (I) is useful also as an agent of improving cerebral functions observed in Alzheimer's disease or senile dementia, through its action on central nervous system, and further has an action of antianxiety and antidepremantia. For such therapeutic use as above, the formulations of this invention using the compound (I) or a salt thereof can be safely administered orally, non-orally, by inhalation, rectally or topically as pharmaceutical compositions or formulations (e.g. powders, granules, tablets, pills, capsules, injections, suppositories, syrups, emulsions, elixir, suspensions and solutions), comprising at least one species of the compounds of this invention alone or in admixture with pharmaceutically acceptable carriers, adjuvants, excipients, vehicles and/or diluents.

Pharmaceutical compositions of the present invention can be formulated in accordance with conventional procedures. In the present specification, "non-orally" includes subcutaneous injection, intravenous injections, intramuscular injection, intraperitoneal injection or instillation. Injectable preparations, for example, sterile injectable aqueous suspensions or oil suspensions can be prepared by known procedure in the fields concerned, using a suitable dispersant or wetting agent and suspending agent. The sterile injections may be in the state of, for example, a solution or a suspension, which is prepared with a non-toxic diluent administrable non-orally, e.g. an aqueous solution, or with a solvent employable for sterile injection. Examples of usable vehicles or acceptable solvents include water, Ringer's solution and an isotonic aqueous saline solution. Further, a sterile non-volatile oil can usually be employed as solvent or suspending agent. Any non-volatile oil and a fatty acid can be used for this purpose, which includes natural, synthetic or semi-synthetic fatty acid oil or fatty acid and natural or synthetic or semi-synthetic mono- or di- or tri-glycerides.

Rectal suppositories can be prepared by mixing the drug with a suitable non-irritable vehicle, for example, cocoa butter and polyethylene glycol, which is in the solid state at ordinary temperatures, in the liquid state at temperatures in intestinal tubes and melts in rectum to release the drug.

As a solid formulation for oral administration, mention is made of powders, granules, tablets, pills and capsules as referred to above. In such formulations as exemplified above, the active component compound can be mixed with at least one additive, for example, sucrose, lactose, cellulose, sugar, mannitol, maltitol, dextran, starch, agar, alginate, chitin, chitosan, pectin, tragacanth gum, gum arabic, gelatin, collagen, casein, albumin, synthetic or semi-synthetic polymer or glyceride. These formulations can contain, as in conventional cases, further additives, for example, an inactive diluent, a lubricant such as magnesium stearate, a preservative such as paraben or sorbic acid, an anti-oxidant such as ascorbic acid, α-tocopherol or cysteine, a disintegrator, a binder, a thickening agent, a buffer, a sweetener, a flavoring agent and a perfuming agent. Tablets and pills can further be prepared with enteric coating. Examples of liquid preparations for oral administration include pharmaceutically acceptable emulsions, syrups, elixirs, suspensions and solutions, which may contain an inactive diluent, for example, water, which is conventionally employed in the field concerned.

The dose of a specific patient is decided depending on the age, body weight, general health conditions, sex, diet, dose interval, administration routes, excretion rate, combinations of drugs and conditions of the diseases then treated, while taking them and any other necessary factors into consideration.

The dose varies with the diseases to be treated, conditions of such diseases, subject patients and administration routes, and it is preferable that a daily dose of 1 to 100 mg (preferably 1 to 50 mg) for oral administration or 0.01 to 50 mg (preferably 0.3 to 30 mg) for intravenous injection is given once or divided into two or three administrations when used as an agent for the therapy of essential hypertension of an adult human.

[WORKING EXAMPLES]

By the following formulation examples, reference examples, working examples and experimental examples, the present invention will be illustrated more concretely, and it is needless to say that they should not be construed as limiting the invention thereto.

Formulation Examples

When the compound (I) of the present invention is used as a therapeutic agent for circulatory disturbances such as hypertension, heart diseases, cerebral apoplexy and nephritis, it can be used in accordance with, for example, the following formulations.

1. Capsules

| | |
|---|---|
| (1) 3-butyl-4-[2'-(2,5-dihydro-5-oxo-1,2,4-oxadiazol-3-yl)biphenyl-4-yl]methylpyrazole-5-carboxylic acid | 10 mg |
| (2) lactose | 90 mg |
| (3) microcrystalline cellulose | 70 mg |
| (4) magnesium stearate | 10 mg |
| one capsule | 180 mg |

(1), (2), (3) and a half of (4) are mixed and then granulated. To the granules is added the remainder of (4), and the whole is filled into a gelatin capsule.

2. Tablets

| | |
|---|---|
| (1) 3-butyl-4-[2'-(2,5-dihydro-5-oxo-1,2,4-oxadiazol-3-yl)biphenyl-4-yl]methylpyrazole-5-carboxylic acid | 10 mg |
| (2) lactose | 35 mg |
| (3) corn starch | 150 mg |
| (4) microcrystalline cellulose | 30 mg |
| (5) magnesium stearate | 5 mg |
| one tablet | 230 mg |

(1), (2), (3), two thirds of (4) and a half of (5) are mixed and then granulated. To the granules are added the remainders of (4) and (5), followed by subjecting the mixture to compression molding.

3. Injections

| | |
|---|---|
| (1) 3-butyl-4-[2'-(2,5-dihydro-5-oxo-1,2,4-oxadiazol-3-yl)biphenyl-4-yl]methylpyrazole-5-carboxylic acid disodium salt | 10 mg |
| (2) inositol | 100 mg |
| (3) benzyl alcohol | 20 mg |
| one ampoule | 130 mg |

(1), (2) and (3) are dissolved in distilled water for injection to make the whole volume 2 ml, which is filled into an ampoule. The whole process is conducted under sterile conditions.

4. Capsules

| | |
|---|---|
| (1) Methyl 3-butyl-4-[2'-(2,5-dihydro-5-oxo-1,2,4-thiadiazol-3-yl)biphenyl-4-yl]methylpyrazole-5-carboxylate | 10 mg |

| | |
|---|---|
| (2) lactose | 90 mg |
| (3) microcrystalline cellulose | 70 mg |
| (4) magnesium stearate | 10 mg |
| one capsule | 180 mg |

(1), (2), (3) and a half of (4) are mixed and then granulated. To the granules is added the remainder of (4), and the whole is filled into a gelatin capsule.

5. Tablets

| | |
|---|---|
| (1) Methyl 3-butyl-4-[2'-(2,5-dihydro-5-oxo-1,2,4-thiadiazol-3-yl)biphenyl-4-yl]methylpyrazole-5-carboxylate | 10 mg |
| (2) lactose | 35 mg |
| (3) corn starch | 150 mg |
| (4) microcrystalline cellulose | 30 mg |
| (5) magnesium stearate | 5 mg |
| one tablet | 230 mg |

(1), (2), (3), two thirds of (4) and a half of (5) are mixed and then granulated. To the granules are added the remainders of (4) and (5), followed by subjecting the mixture to compression molding.

6. Injections

| | |
|---|---|
| (1) Methyl 3-butyl-4-[2'-(2,5-dihydro-5-oxo-1,2,4-thiadiazol-3-yl)biphenyl-4-yl]methylpyrazole-5-carboxylate sodium salt | 10 mg |
| (2) inositol | 100 mg |
| (3) benzyl alcohol | 20 mg |
| one ampoule | 130 mg |

(1), (2) and (3) are dissolved in distilled water for injection to make the whole volume 2 ml, which is filled into an ampoule. The whole process is conducted under sterile conditions.

7. Capsules

| | |
|---|---|
| (1) 3-butyl-1-(2-chlorophenyl)-4-[2'-(2,5-dihydro-5-oxo-1,2,4-oxadiazol-3-yl)biphenyl-4-yl]methylpyrazol-5-carboxylic acid | 10 mg |
| (2) lactose | 90 mg |
| (3) microcrystalline cellulose | 70 mg |
| (4) magnesium stearate | 10 mg |
| one capsule | 180 mg |

(1), (2), (3) and a half of (4) are mixed and then granulated. To the granules is added the remainder of (4), and the whole is filled in a gelatin capsule.

8. Tablets

| | |
|---|---|
| (1) 3-butyl-1-(2-chlorophenyl)-4-[2'-(2,5-dihydro-5-oxo-1,2,4-oxadiazol-3-yl)biphenyl-4-yl]methylpyrazole-5-carboxylic acid | 10 mg |
| (2) lactose | 35 mg |
| (3) corn starch | 150 mg |
| (4) microcrystalline cellulose | 30 mg |
| (5) magnesium stearate | 5 mg |
| one tablet | 230 mg |

(1), (2), (3), two thirds of (4) and a half of (5) are mixed and then granulated. To the granules are added the remainders of (4) and (5), followed by subjecting the mixture to compression molding.

9. Injections

| | |
|---|---|
| (1) 3-butyl-1-(2-chlorophenyl)-4-[2'-(2,5-dihydro-5-oxo-1,2,4-oxadiazol-3-yl)biphenyl-4-yl]methylpyrazole-5-carboxylic acid disodium salt | 10 mg |
| (2) inositol | 100 mg |
| (3) benzyl alcohol | 20 mg |
| one ampoule | 130 mg |

(1), (2) and (3) are dissolved in distilled water for injection to make the whole volume 2 ml, which is filled into an ampoule. The whole process is conducted under sterile conditions.

10. Capsules

| | |
|---|---|
| (1) 3-butyl-1-(2-chlorophenyl)-4-[2'-(2,5-dihydro-5-oxo-1,2,4-thiadiazol-3-yl)biphenyl-4-yl]methylpyrozole-5-carboxylic acid | 10 mg |
| (2) lactose | 90 mg |
| (3) microcrystalline cellulose | 70 mg |
| (4) magnesium stearate | 10 mg |
| one capsule | 180 mg |

(1), (2), (3) and a half of (4) are mixed and then granulated. To the granules is added the remainder of (4), and the whole is filled into a gelatin capsule.

11. Tablets

| | |
|---|---|
| (1) 3-butyl-1-(2-chlorophenyl)-4-[2'-(2,5-dihydro-5-oxo-1,2,4-thiadiazol-3-yl)biphenyl-4-yl]methylpyrazole-5-carboxylic acid | 10 mg |
| (2) lactose | 35 mg |
| (3) corn starch | 150 mg |
| (4) microcrystalline cellulose | 30 mg |
| (5) magnesium stearate | 5 mg |
| one tablet | 230 mg |

(1), (2), (3), two thirds of (4) and a half of (5) are mixed and then granulated. To the granules are added the remainders of (4) and (5), followed by subjecting the mixture to compression molding.

12. Injections

| | |
|---|---|
| (1) 3-butyl-1-(2-chlorophenyl)-4-[2'-(2,5-dihydro-5-oxo-1,2,4-thiadiazol-3-yl)biphenyl-4-yl]methylpyrazole-5-carboxylic acid disodium salt | 10 mg |
| (2) inositol | 100 mg |
| (3) benzyl alcohol | 20 mg |
| one ampoule | 130 mg |

(1), (2) and (3) are dissolved in distilled water for injection to make the whole volume 2 ml, which is filled into an ampoule. The whole process is conducted under sterile conditions.

Reference Example 1

4-Methylbiphenyl-2'-carboxamidoxime

To a solution of hydroxylamine hydrochloride (17.9 g) in dimethyl sulfoxide (120 ml) was added a methanol solution of sodium methoxide prepared from metallic sodium (5.92 g) and anhydrous methanol (50 ml). The mixture was stirred for 10 minutes at room temperature, to which was added 2'-cyano-4-methylbiphenyl (10 g). The reaction mixture was stirred for 5 hours at 100° C. After cooling, the reaction mixture was distributed into ethyl acetate and water, and the aqueous layer was subjected to extraction with ethyl acetate. The organic layers were combined, washed with water and dried, then the solvent was distilled off under reduced pressure. The residue was purified by column chromatography on silica gel to afford the title compound as white amorphous product (11.2 g, 96%).

$^1$H-NMR (200 MHz, CDCl$_3$) δ : 2.39(3H,s), 4.42(2H,br s), 7.22(2H,d), 7.31–7.50(5H,m), 7.56–7.60(1H,m). IR (KBr) cm$^{-1}$: 3490, 3380, 1642, 1575, 1568.

Reference Example 2

5-Trichloromethy-1-3-(4'-methylbiphenyl-2-yl)-1,2,4-oxadiazole

To a benzene (100 ml) solution of the compound (10 g) obtained in Reference Example 1 was added dropwise trichloroacetic anhydride (16.4 g). The reaction mixture was then heated under reflux for two hours. The reaction mixture was cooled, which was then concentrated to dryness. The concentrate was distributed into ether and water. The aqueous layer was subjected to extraction with ether. The extract was combined with the organic layer, which was washed with water and dried, then the solvent was distilled off under reduced pressure. The residue was purified by column chromatography on silica gel to afford the title compound as a pale yellow oily product (12 g, 77%).

$^1$H-NMR (200 MHz,CDCl$_3$) δ : 2.38(3H,s), 7.16(4H,s), 7.44–7.64(3H,m), 7.88–7.93(1H,m). IR (neat) cm$^{-1}$: 3025, 1600, 1580, 1561, 1508.

Reference Example 3

5-Trichloromethyl-3-(4'-bromomethylbiphenyl-2-yl)-1,2,4-oxadiazole

To a carbon tetrachloride (300 ml) solution of the compound (24.8 g) obtained in Reference Example 2, were added N-bromosuccinimide (12.5 g) and α, α'-azobisisobutyronitrile (1.15 g). The mixture was heated for two hours under reflux, which was then cooled. White insolubles were filtered off, and the filtrate was diluted with dichloromethane. The organic layer was washed with water and dried, then the solvent was distilled off under reduced pressure. The residue was recrystallized from ether-hexane to afford the the title compound as colorless crystals (23.0 g, 76%), m.p. 77°–79° C.

|         | C(%)   | H(%)  | N(%)  |
|---------|--------|-------|-------|
| Calcd.: | 43.52; | 2.51; | 6.34  |
| Found:  | 43.76; | 2.33; | 6.31  |

$^1$H-NMR (200 MHz,CDCl$_3$) δ: 4.52(2H,s), 7.23(2H,d), 7.38(2H,d), 7.44–7.65(3H,m), 7.91–7.95(1H,m). IR (KBr) cm$^{-1}$: 1600, 1560, 1475, 1428, 1332.

Reference Example 4

4'-Bromomethylbiphenyl-2-carboxamide

4'-Methylbiphenyl-2-carboxamide (2.1 g), N-bromosuccinimide (2.5 g) and azobisisobutyronitrate (AIBN: 82 mg) were added benzene (20 ml), then the mixture was stirred for 20 hours at 60°–70° C. Resulting crystalline precipitates were collected by filtration and washed with isopropyl ether, which were suspended in water. The suspension was stirred for 30 minutes. Insoluble material was collected by filtration and dried. Crude crystals thus obtained were recrystallized from ethyl acetate—methanol to afford colorless needles (1.6 g, 55%), m.p. 220°–221° C. (d).

|         | C(%)   | H(%)  | N(%)  |
|---------|--------|-------|-------|
| Calcd.: | 57.95; | 4.17; | 4.83  |
| Found:  | 57.85; | 4.16; | 4.77  |

$^1$H-NMR (200 MHz, DMSO-d$_6$) δ: 4.75(2H,s), 7.31–7.69 (10H,m). IR (KBr) cm$^{-1}$: 3150, 3000, 1570, 1540, 1520, 1500, 1300, 665.

Working Example 1

Methyl 3-butyl-4-[2'-(2,5-dihydro-5-oxo-1,2,4-oxadiazol-3-yl) biphenyl-4-yl]methylpyrazole-5-carboxylate a) Ethyl 2-methoxyimino-4-oxooctanoate To an ethanol (100 ml) solution of ethyl 2,4-dioxooctanoate (20 g) (K. Seki et al., Chem. Pharm. Bull., 32, 1568(1984)) was added, under ice-cooling, methoxyamine hydrochloride (8.4 g), and the mixture was stirred for one hour, then it was stirred for further 15 hours at room temperature. The reaction mixture was concentrated under reduced pressure, to which was added a saturated aqueous solution of sodium hydrogencarbonate, followed by extraction with ether. The extract solution was dried over anhydrous sodium sulfate, then the solvent was distilled off under reduced pressure. The residue was purified by column chromatography on silica gel to afford the title compound as a colorless oil (16.6 g, 72%).

$^1$H-NMR(200 MHz,CDCl$_3$) δ: 0.91(3H,t), 1.23–1.41(2H, m), 1.50–1.64(2H,m), 2.47(2H,t), 3.70(2H,s), 4.06(3H,s), 4.36(2H,q). IR(neat)cm$^{-1}$: 2960, 2935, 1720, 1340, 1125, 1045.

b) Ethyl 3-(2'-cyanobiphenyl-4-yl)methyl-2-methoxyimino-4-oxooctanoate

A mixture of the compound (10.8 g) obtained in Working Example 1 a), 4-bromomethyl-2'-cyanobiphenyl (12.2 g), anhydrous potassium carbonate (13.8 g) and dimethylformamide (100 ml) was stirred for 20 hours at room temperature. To the reaction mixture was added water (1.5 liter), which was subjected to extraction with ethyl acetate. The extract solution was dried over anhydrous sodium sulfate, then the solvent was distilled off under reduced pressure. The residue was purified by column chromatography on silica gel to afford the title compound as a colorless oil (10.7 g, 57%).

$^1$H-NMR(200 MHz,CDCl$_3$) δ: 0.89(3H,t), 1.20–1.36(5H, m), 1.49–1.63(2H,m), 2.34(2H,t), 3.00(1H,dd), 3.46(1H, dd), 3.97(3H,s), 4.19–4.33(3H,m), 7.25(2H,d), 7.37–7.50 (4H,m), 7.62(1H,m), 7.74(1H,d). IR(neat)cm$^-$: 2955, 2940, 2220, 1720, 1480, 1245, 1045, 765.

c) Ethyl 3-butyl-4-(2'-cyanobiphenyl-4-yl) methylpyrazole-5-carboxylate

A mixture of the compound (2.8 g) obtained in Working Example 1 b), hydrazine.monohydrate (1 g), acetic acid (30 ml) and 2-methoxyethanol (15 ml) was stirred for 60 hours at 105° C. The reaction mixture was concentrated under reduced pressure, to which was added a saturated aqueous solution of sodium hydrogencarbonate, followed by extraction with ether. The extract was dried over anhydrous sodium sulfate, then the solvent was distilled off under reduced pressure. The residue was purified by column chromatography on silica gel to afford the title compound as pale yellow powder (1.4 g, 55%).

$^1$H-NMR(200 MHz,CDCl$_3$) δ: 0.88(3H,t), 1.23–1.40(5H, m), 1.50–1.63(2H,m), 2.61(2H,t), 4.19(2H,s), 4.35(2H,q), 7.26(2H,d), 7.38–7.50(4H,m), 7.63(1H,dd), 7.74(1H,d). IR(nujol)cm$^{-1}$: 3400, 3230, 2225, 1700, 1445, 1145.

d) Ethyl 3-butyl-4-(2'-hydroxycarbamimidoylbiphenyl-4-yl) methylpyrazole-5-carboxylate A mixture of the compound (1.4 g) obtained in Working Example 1 c), hydroxylamine hydrochloride (2.5 g), triethylamine (3.3 g) and dimethyl sulfoxide (35 ml) was stirred for 90 hours at 70° C. To the reaction mixture was added water (300 ml), which was subjected to extraction with ethyl acetate. The extract solution was dried over anhydrous sodium sulfate, then the solvent was distilled off under reduced pressure to leave the title compound as pale yellow powder (1.4 g, 91%).

$^1$H-NMR(200 MHz,CDCl$_3$) δ: 0.85(3H,t), 1.20–1.37(5H, m), 1.44–1.68(2H,m), 2.56(2H,t), 4.14(2H,s), 4.34(2H,q), 4.41(2H,brs), 7.15–7.59(7H,m), 7.78(1H,d). IR(nujol)cm$^{-1}$: 3180, 1710, 1655, 1650, 1045.

e) Methyl 3-butyl-4-[2'-(2,5-dihydro-5-oxo-1,2,4-oxadiazol-3-yl) biphenyl-4-yl]methylpyrazole-5-carboxylate To a dichloromethane (15 ml) solution of the compound (0.65 g) obtained in Working Example 1 d) and triethylamine (0.11 g) was added dropwise, under ice-cooling, a dichloromethane (2 ml) solution of methyl chloroformate (0.11 g). The mixture was stirred for 30 minutes, then the reaction mixture was washed with water and dried over anhydrous sodium sulfate. The solvent was distilled off under reduced pressure, and the residue was purified by column chromatography on silica gel to afford pale yellow powder (0.47 g).

This pale yellow powder (0.47 g) and 1,8-diazabicyclo [5.4.0]-7-undecene (0.46 g) were added to ethyl acetate (7 ml). The mixture was heated for 2 hours under reflux. The reaction mixture was washed with dilute hydrochloric acid and dried over anhydrous sodium sulfate. The solvent was distilled off under reduced pressure. The residue was stirred, in methanol (40 ml), together with a 28% sodium methoxide methanol solution (0.30 g), for 24 hours at room temperature. The reaction mixture was concentrated under reduced pressure, to which was added water, followed by extraction with ethyl acetate. The extract solution was dried over anhydrous sodium sulfate, then the solvent was distilled off under reduced pressure. The residue was recrystallized from ethyl acetate—isopropyl ether to afford the title compound as colorless needles (0.33 g, 50%), m.p.194°–195° C.

|  | C(%) | H(%) | N(%) |
|---|---|---|---|
| Calcd.: | 66.55; | 5.59; | 12.95 |
| Found: | 66.72; | 5.64; | 12.94 |

$^1$H-NMR(200 MHz,CDCl$_3$) δ: 0.88(3H,t), 1.20–1.40(2H, m), 1.44–1.60(2H,m), 2.55(2H,t), 3.74(3H,s), 4.12(2H,s), 7.16(2H,d), 7.21(2H,d), 7.40–7.65(3H,m), 7.85(1H,d). IR(nujol)cm$^{-1}$: 3250, 1755, 1710, 1455.

Working Example 2

3-Butyl-4-[2'-(2,5-dihydro-5-oxo-1,2,4-oxadiazol-3-yl) biphenyl-4-yl]methylpyrazole-5-carboxylic acid A methanol (2 ml) solution of the compound (0.23 g) obtained in Working Example 1 e) and 1N sodium hydroxide (1 ml) was stirred for 20 hours at 50° C. The reaction mixture was concentrated under reduced pressure, to which were added water (10 ml) and 2N HCl (1 ml), followed by extraction with chloroform. The extract was dried over anhydrous sodium sulfate, then the solvent was distilled off under reduced pressure. The residue was recrystallized from ethyl acetate to afford the title compound as colorless prisms (0.16 g, 72%), m.p.213°–214° C.

|  | C(%) | H(%) | N(%) |
|---|---|---|---|
| Calcd.: | 66.02; | 5.30; | 13.39 |
| Found: | 65.79; | 5.23; | 13.20 |

$^1$H-NMR(200 MHz,CDCl$_3$) δ: 0.88(3H,t), 1.22–1.40(2H, m), 1.46–1.63(2H,m), 2.58(2H,t), 4.16(2H,s), 7.24(4H,s), 7.40–7.68(4H,m). IR(nujol)cm$^{-1}$: 3175, 1800, 1690.

Working Example 3

Methyl 3-butyl-4-[2'-(2,5-dihydro-5-oxo-1,2,4-thiadiazol-3-yl) biphenyl-4-yl]methylpyrazole-5-carboxylate A dichloromethane (15 ml) solution of the compound (0.80 g) obtained in Working Example 1 d) was added dropwise, under ice-cooling, to a dichloromethane (5 ml) solution of 1,1'-dithiocarbonyldiimidazole (0.24 g), then the mixture was stirred for one hour. To the reaction mixture were added silica gel (Merck, Art7734, 6 g), chloroform (80 ml) and methanol (2 ml). The mixture was stirred for 3 hours at room temperature. The silica gel was filtered off and was washed with a mixture of chloroform and methanol (5:1), and the filtrate was concentrated under reduced pressure. The concentrate was stirred, together with a 28% sodium methoxide methanol solution (0.30 g), in methanol (25 ml) for 60 hours at room temperature. The reaction mixture was concentrated under reduced pressure, to which was added water, followed by extraction with ethyl acetate. The extract was dried over anhydrous sodium sulfate, then the solvent was distilled off under reduced pressure. The residue was purified by column chromatography on silica gel, followed by recrystallization from isopropyl ether to afford the title compound as colorless prisms (0.28 g, 33%), m.p.171°–172° C.

|  | C(%) | H(%) | N(%) |
|---|---|---|---|
| Calcd.: | 64.27; | 5.39; | 12.49 |
| Found: | 64.35; | 5.36; | 12.61 |

$^1$H-NMR(200 MHz,CDCl$_3$) δ: 0.87(3H,t), 1.20–1.40(2H, m), 1.43–1.58(2H,m), 2.48(2H,t), 3.70(3H,s), 4.10(2H,s), 7.13(2H,d), 7.16(2H,d), 7.38–7.62(3H,m), 7.87(1H,d), 9.90(1H,brs). IR(nujol)cm$^{-1}$: 3260, 1715, 1705, 1670.

Working Example 4

3-Butyl-4-[2,5-dihydro-5-oxo-1,2,4-thiadiazol-3-yl) biphenyl-4-yl]methylpyrazole-5-carboxylic acid Starting from the compound (0.23 g) obtained in Working Example 3, substantially the same reaction as in Working Example 2 was conducted to give the title compound as colorless prisms (0.19 g, 85%), m.p.202°–203° C. (ethyl acetate).

|  | C(%) | H(%) | N(%) |
|---|---|---|---|
| Calcd.: | 63.58; | 5.10; | 12.89 |
| Found: | 63.35; | 5.24; | 12.61 |

$^1$H-NMR(200 MHz,CDCl$_3$) δ0.87(3H,t), 1.21–1.40(2H, m), 1.45–1.60(2H,m), 2.55(2H,t), 4.15(2H,s), 7.19(4H,s), 7.37–7.62(4H,m), 11.90(1H,brs). IR(nujol)cm$^{-1}$: 3190, 3120, 3060, 1680, 1415, 1265, 1150.

Working Example 5

Methyl 3-butyl-1-1-(2-chlorophenyl)-4-[2'-92,5-dihydro-5-oxo-1,2, 4thiadiazol-3-yl)biphenyl-4-yl] methylpyrazole-5-carboxylate a) Ethyl 3-butyl-1-(2-chlorophenyl)-4-(2'-cyanobiphenyl-4-yl) methylpyrazole-5-carboxylate Starting from the compound (1.6 g) obtained in Working Example 1 b) and 2-chlorophenylhydrazine hydrochloride (2.2 g), substantially the same reaction as in Working Example 1 c) was conducted to afford the title compound as an orange oil (1.2 g, 65%).

$^1$H-NMR(200 MHz,CDCl$_3$) δ: 0.87(3H,t), 1.01(3H,t), 1.25–1.43(2H,m), 1.54–1.68(2H,m), 2.64(2H,t), 4.12(2H,q), 4.25(2H,s), 7.30(2H,d), 7.36–7.51(8H,m), 7.63(1H,dd), 7.76(1H,d). IR(neat)cm$^-$: 2950, 2925, 2220, 1720, 1490, 1235, 760 b) Ethyl 3-butyl-1-(2-chlorophenyl)-4-(2'-hydroxycarbaminidoylbipheyl-4-yl)methylpyrazole-5-carboxylate Starting from the compound (1.2 g) obtained in Working Example 5 a), substantially the same reaction as in Working Example 1 d) was conducted to afford the title compound as an orange oil (0.57 g, 45%).

$^1$H-NMR(200MHz,CDCl$_3$) δ: 0.87(3H,t), 1.01(3H,t), 1.23–1.43 (2H,m), 1 .50–1.65(2H,m), 2.62(2H,t), 4.12(2H, q), 4.23(2H,s), 4 .41(2H,brs), 7.23(2H,d), 7.33–7.60(10H, m). IR(nujol)cm$^{-1}$: 3380, 1720, 1650, 1495, 1240.

c) Methyl 3 -butyl-1-(2-chlorophenyl)-4-[2'-(2,5-dihydro-5-oxo-1,2,4-oxadiazol-3-yl)biphenyl-4-yl]methylpyrazole-5-carboxylate Starting from the compound (0.30 g) obtained in Working Example 5 b), substantially the same reaction as in Working Example 1 e) was conducted to afford the title compound as a yellow oily product (0.20 g, 65%).

|        | C(%)  | H(%) | N(%)  |
|--------|-------|------|-------|
| Calcd.:| 66.17;| 5.08;| 10.15 |
| Found: | 66.00;| 5.08;| 10.12 |

$^1$H-NMR(200MHz,CDCl$_3$) δ: 0.88(3H,t), 1.26–1.45(2H, m), 1.52–1.70(2H,m), 2.6 3(2H,t), 3.63(2H,t), 3.67(3H,s), 4.22(2H,s), 7.27(4H, s), 7.36–7.62(7H,m), 7.88(1H,d) IR(neat)cm$^{-1}$: 2955, 1785, 1730, 1490, 1440, 1240, 760, 1785, 1730, 1490, 1440, 1240, 760, 730.

Working Example 6

3-Butyl-1-(2-chlorophenyl)-4-[2'-(2,5-dihydro-5-oxo-1,2,4oxadiazol-3yl) biphenyl-4-yl]methylpyrazole-5-carboxylic acid Starting from the compound (0.16 g) obtained in Working Example 5 c), substantially the same reaction as in Working Example 2 was conducted to afford the title compound as yellow powder (0.10 g, 63%).

|        | C(%)  | H(%) | N(%)  |
|--------|-------|------|-------|
| Calcd.:| 64.24;| 4.69;| 10.26 |
| Found: | 64.14;| 4.69;| 10.30 |

$^1$H-NMR(200 MHz,CDCl$_3$) δ: 0.92(3H,t), 1.31–1.50(2H, m), 1.60–1.75(2H,m), 2.72(2H,t), 4.15(2H,s), 7.18(4H,s), 7.30–7.66(7H,m), 7.90(1H,d). IR(nujol)cm$^{-1}$: 1765,1720, 1490, 765.

Working Example 7

Methyl 3-butyl-1-(2-chlorophenyl)-4-[2'-(2,5-dihydro-5-oxo-1,2,4-thiadiazol-3-yl) biphenyl-4-yl]methylpyrazole-5-carboxylate Starting from the compound (0.27 g) obtained in Working Example 5 b), substantially the same reaction as in Working Example 3 was conducted to afford the title compound as an orange oil (0.13 g, 46%).

|        | C(%)  | H(%) | N(%)  |
|--------|-------|------|-------|
| Calcd.:| 64.45;| 4.87;| 10.02 |
| Found: | 64.26;| 4.90;| 10.13 |

$^1$H-NMR(200 MHz,CDCl$_3$) δ: 0.88(3H,t), 1.26–1.45(2H, m,) 1.53–1.70(2H,m), 2.63(2H,t), 3.67(3H,s), 7.25(4H,s), 7.36–7.60(7H,m), 7.90(1H,d), 8.28(1H,brs). IR(neat)cm$^{-1}$: 2955, 1725, 1700, 1670, 760.

Working Example 8

3-Butyl-1-(2-chlorophenyl),4-[2'-(2,5-dihydro-5-oxo-1,2,4-thiadiazol-3-yl) biphenyl-4-yl]methylpyrazole-5-carboxylic acid Starting from the compound (0.10 g) obtained in Working Example 7, substantially the same reaction as in Working Example 2 was conducted to afford the title compound as pale yellow powder (80 mg, 82%).

|        | C(%)  | H(%) | N(%)  |
|--------|-------|------|-------|
| Calcd.:| 63.90;| 4.62;| 10.28 |
| Found: | 63.81;| 4.76;| 10.25 |

$^1$H-NMR(200 MHz,CDCl$_3$) δ: 0.93(3H,t), 1.32–1.50(2H, m), 1.60–1.75(2H,m), 2.74(2H,t), 4.19(3H, s), 7.15(2H,d), 7.24(2H,d), 7.30–7.60(7H,m), 8.00(1H, d), 8.38(1H,brs). IR(nujol)cm$^{-1}$: 1700, 1670, 1490, 765.

Experimental Example 1

Inhibitory Effect of Binding of Anqiotensin-II to Angiotensin Receptor

[Method]

An experiment of inhibition on the binding of angiotensin II (AII) to AII receptor was conducted by modifying the method of Douglas et al. [Endocrinology, 102, 685-696 (1978)]. An AII receptor membrane fraction was prepared from bovine adrenal cortex.

The compound of the present invention ($10^{-6}$M or $10^{-7}$M) and $^{125}$I-angiotensin II ($^{125}$I-AII) (2.44kBq/50 μl) were added to the receptor membrane fraction, and the mixture was incubated at room temperature for one hour. The receptor-bound and free $^{125}$I-AII were separated through a filter (Whatman GF/B filter), and the radioactivity of $^{125}$I-AII bound to the receptor was determined.

[Results]

The results relating to the compounds of the present invention are shown in Table 1.

Experimental Example 2

Inhibitory Effect of the Compound of the Present Invention on Pressor Action of AII

[Method]

Jcl:SD rats (9 week old, male) were used. On the previous day of the experiment, these animals were applied with cannulation into the femoral artery and vein under anesthesia with pentobarbital Na. These animals were fasted but allowed to access freely to drinking water until the experiment was started. Just on the day of conducting the experiment, the artery cannula was connected with a blood-pressure transducer, and the average blood pressure was recorded by means of polygraph. Before administration of the drug, the pressor action due to intravenous administration of AII (100 ng/kg) as the control was determined. The drugs were orally administered, then, at each point of the determination, AII was administered intravenously, and the pressor action was similarly determined. By comparing the pressor action before and after administration of the drug, the percent inhibition by the drug was evaluated.

[Results]

The results relating to the compounds of the present invention are shown in Table 1.

TABLE 1

| W. Ex. No. | Chemical Formula | Binding-inhibitory action (rate) % | Pressor-inhibitory action a) 1 mg/kg · p.o. |
|---|---|---|---|
| 2 | 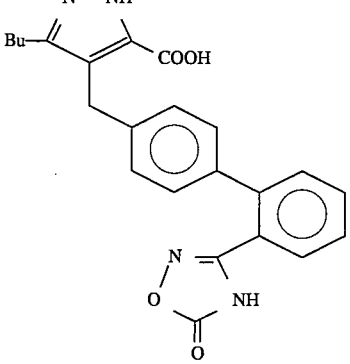 | 68 ($10^{-6}$M) <br> 30 ($10^{-7}$M) | + |
| 3 | 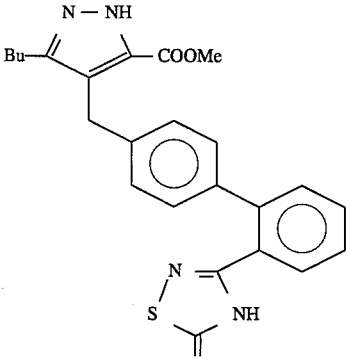 | 17 ($10^{-6}$M) <br> 7 ($10^{-7}$M) | +++ |

TABLE 1-continued

| W. Ex. No. | Chemical Formula | Binding-inhibitory action (rate) % | Pressor-inhibitory action a) 1 mg/kg · p.o. |
|---|---|---|---|
| 6 | (structure: 2-Cl-phenyl-N=N-pyrazole with Bu, COOH, CH₂-biphenyl-oxadiazolone) | 32 (10⁻⁶M) | ++ |
| 8 | (structure: 2-Cl-phenyl-N=N-pyrazole with Bu, COOH, CH₂-biphenyl-thiadiazolone) | 37 (10⁻⁶M) | +++ | a) +++ ≧ 70% > ++ ≧ 50% > +

What is claimed is:

1. A compound represented by the formula:

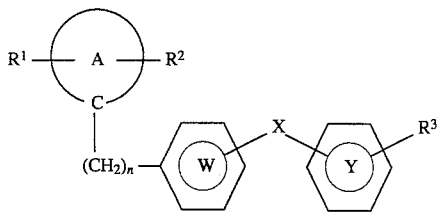

wherein:
the ring A stands for a 5–10 membered aromatic heterocyclic group optionally having, besides $R^1$ and $R^2$, a further substituent selected from the group consisting of halogen, nitro, cyano, amino, N-lower ($C_{1-4}$) alkylamino, N,N-di-lower ($C_{1-4}$) akylamino, phenylamino, morpholino, piperidino, piperazino, N-phenylpiperazino, and a group represented by the formula —U—$R^6$, wherein:
U is selected from the group consisting of a bond —O—, —S— and —CO—, and $R^6$ is selected from the group consisting of hydrogen, a lower ($C_{1-4}$) alkyl group and a phenyl group, wherein said lower alkyl group may optionally be substituted with hydroxyl, amino, halogen, nitro, cyano, or lower ($C_{1-4}$) alkoxy, and wherein said phenyl group may optionally be substituted with one or two of hydroxyl, amino, N-lower ($C_{1-4}$) alkylamino, N,N-lower ($C_{1-4}$) alkylamino, acetylamino, halogen, nitro, cyano, lower ($C_{1-4}$) alkyl, lower ($C_{1-4}$) alkoxy, lower ($C_{1-4}$) alkylthio, or acetyl;

$R^1$ stands for an optionally substituted hydrocarbon residue selected from the group consisting of
(i) an alkyl, alkenyl, alkynyl or cycloalkyl group which may be substituted with hydroxy, amino, N-lower ($C_{1-4}$) alkylamino, N,N-di-lower ($C_{1-4}$) alkylamino, halogen, lower ($C_{1-4}$) alkoxy or lower ($C_{1-4}$) alkylthio, and
(ii) a phenyl or phenyl-lower ($C_{1-4}$) alkyl group which may be substituted with halogen, nitro, amino, N-lower ($C_{1-4}$) alkylamino, N,N-di-lower ($C_{1-4}$) alkylamino, lower ($C_{1-4}$) alkoxy, lower ($C_{1-4}$) alkylthio, or lower ($C_{1-4}$) alkyl, which hydrocarbon residue is optionally bonded through a group selected from the group consisting of —O—; —S(O)$_m$—, wherein m is an integer from 0 to 2; and a group of the formula —N(R$^9$)—, wherein R$^9$ is hydrogen or lower (C$_{1-4}$) alkyl;

R$^2$ stands for an optionally esterified carboxyl group;

R$^3$ stands for a group of the formula:

$$\underset{j-i}{HN\diagdown\diagup N}$$

wherein i is —O— or —S— and j is elected from the group consisting of a carbonyl group, a thiocarbonyl group, and an optionally oxidized sulfur atom or a group convertible thereto;

X is a direct bond, the ring W is a phenylene group, the ring Y is a phenylene group, and n denotes an integer of 1 to 3, or a salt thereof.

2. A compound according to claim 1, wherein the ring A is a 5-, 6-, 8-, 9- or 10- membered aromatic heterocyclic group.

3. A compound according to claim 2, wherein the ring A is a monocyclic ring.

4. A compound according to claim 2, wherein the ring A is selected from the group consisting of

[chemical structures]

5. A compound according to claim 1, wherein R$^1$ is lower (C$_{1-8}$) alkyl, lower (C$_{2-8}$) alkenyl or lower (C$_{3-6}$) cycloalkyl which may be bound through a group of the formula: —N(R$^9$)— wherein R$^9$ is hydrogen or lower (C$_{1-4}$) alkyl, —O— or —S(O)$_m$— wherein m is an integer of 0 to 2 and which may be substituted with hydroxy, amino, N-lower (C$_{1-4}$)) alkylamino, N,N-dilower (C$_{1-4}$) alkylamino, halogen, lower (C$_{1-4}$) alkoxy or lower (C$_{1-4}$) alkylthio.

6. A compound according to claim 1, wherein R$^1$ is alkyl or alkenyl which is bound through a group of the formula: —N(R$^9$)— wherein R$^9$ is hydrogen or lower (C$_{1-4}$) alkyl, —O— or —S(O)$_m$— wherein m is an integer of 0 to 2 and which may be substituted with hydroxy, optionally substituted amino, halogen, lower (C$_{1-4}$) alkoxy or lower (C$_{1-4}$) alkylthio.

7. A compound according to claim 1, wherein R$^1$ is selected from the class consisting of methylamino, ethylamino, propylamino, propenylamino, isopropylamino, allylamino, butyrylamino, isobutyrylamino, dimethylamino, methylethylamino, methoxy, ethoxy, propoxy, isopropoxy, propenyloxy, allyloxy, butoxy, isobutoxy, sec-butoxy, t-butoxy, 2-butenyloxy, 3-butenyloxy, isobutenyloxy, pentoxy, isopentoxy, hexyloxy, methylthio, ethylthio, propylthio, isopropylthio, allylthio, butylthio, isobutylthio, secbutylthio, t-butylthio, 2-butenylthio, 3-butenylthio, isobutenylthio, pentylthio, isopentylthio and hexylthio.

8. A compound according to claim 1, wherein R$^2$ is selected from the class consisting of —COOH and a salt thereof, —COOMe, —COOEt, —COOtBu, —COOPr, pivaloyloxymethoxycarbonyl, 1-(cyclohexyloxycarbonyloxy)ethoxycarbonyl, (5-methyl-2-oxo-1,3-dioxolen-4-yl) methoxycarbonyl, acetoxymethyloxycarbonyl, propionyloxymethoxycarbonyl, n-butyryloxymethoxycarbonyl, isobutyryloxymethoxycarbonyl, 1-(ethoxycarbonyloxy)ethoxycarbonyl, 1(acetyloxy)ethoxycarbonyl, 1-isobutyryloxy) ethoxycarbonyl, cyclohexylcarbonyloxymethoxycarbonyl, benzoyloxymethoxycarbonyl, cinnamyloxycarbonyl and cyclopentylcarbonyloxymethoxycarbonyl.

9. A compound according to claim 1, wherein R$^3$ is a 2,5-dihydro-5-oxo-1,2,4-oxadiazol-3-yl group.

10. A compound according to claim 1, wherein R$^3$ is a 2,5-dihydro-5-oxo-1,2,4-thiadiazol-3-yl group.

11. A compound according to claim 1, wherein R$^3$ is a 2,5-dihydro-5-thioxo-1,2,4-oxadiazol-3-yl group.

12. A compound according to claim 1, wherein n is 1.

13. A compound according to claim 1, wherein R$^1$ is alkyl, alkenyl, alkynyl or cycloalkyl which may be bound through a group of the formula: —N(R$^9$)— wherein R$^9$ is hydrogen or lower (C$_{1-4}$) alkyl, —O— or —S(O)$_m$— m is an integer of 0 to 2 and which may be substituted with hydroxy, optionally substituted amino, halogen, lower (C$_{1-4}$) alkoxy or lower (C$_{1-4}$) alkylthio.

14. A compound represented by the formula,

[chemical structure]

wherein the ring A is selected from the class consisting of

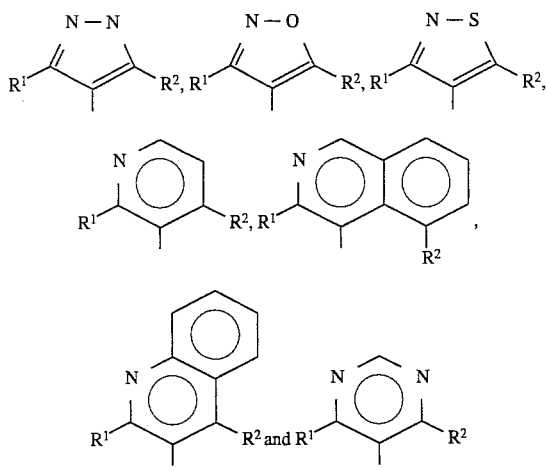

$R^1$ may be bonded through a hetero atom and stands for an optionally substituted lower ($C_{1-6}$) alkyl; $R^2$ stands for a group represented by the formula —CO—D", wherein D" stands for hydroxyl group, amino, N-lower ($C_{1-4}$) alkylamino, N,N-di-lower ($C_{1-4}$) alkylamino or a lower ($C_{1-4}$) alkoxy whose alkyl moiety is optionally substituted with hydroxyl group, amino, halogen, a lower ($C_{2-6}$) alkanoyloxy, lower ($C_{3-7}$) cycloalkanoyloxy, 1-lower ($C_{1-6}$) alkoxycarbonyloxy, lower ($C_{3-7}$) cycloalkoxycarbonyloxy or a lower ($C_{1-4}$) alkoxy; $R^3$ stands for groups represented by the formula,

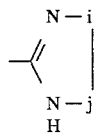

wherein i stands for —O— or —S—; j stands for >=O, >=S or >S(O)$_m$; and m is of the same meaning as defined above, which are optionally protected with optionally substituted lower ($C_{1-4}$) alkyl or an acyl group.

15. An angiotensin II antagonistic agent containing a compound or a salt thereof claimed in claim 1.

16. A method for the prophylaxis or treatment of hypertension in a mammal by administering an antihypertensive amount of an agent of claim 15 to a mammal in need thereof.

17. An angiotensin II antagonistic agent containing a compound or a salt thereof claimed in claim 14.

18. A compound represented by the formula:

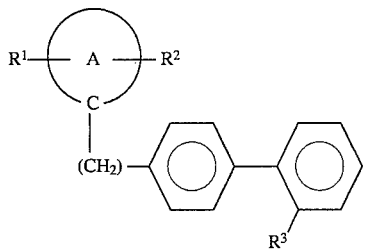

wherein the ring A stands for a pyrazole or pyridine ring optionally having, besides $R^1$ and $R^2$, a further substituent selected from the group consisting of halogen, nitro, cyano, an optionally substituted amino group and a group represented by the formula —U—$R^6$, wherein U is selected from the group consisting of a bond, —O—, —S— and —CO—, and wherein $R^6$ is selected from the group consisting of hydrogen, an optionally substituted lower alkyl group and an optionally substituted phenyl group;

$R^1$ stands for an optionally substituted hydrocarbon residue selected from the group consisting of
(i) an alkyl, alkenyl, alkynyl or cycloalkyl group which may be substituted with hydroxy, optionally substituted amino, halogen, lower (C1–4) alkoxy or lower (C1–4) alkylthio and
(ii) an aryl or aralkyl group which may be substituted with halogen, nitro, optionally substituted amino, lower (C1–4) alkoxy, lower (C1–4) alkylthio or lower (C1–4) alkyl, which hydrocarbon residue is optionally bonded through a group of the formula —N($R^9$)—, wherein $R^9$ is selected from the group consisting of hydrogen, lower (C1–4) alkyl, —O— and —S(O)m—, wherein m is an integer from 0 to 2;

$R^2$ stands for an optionally esterified carboxyl group;

$R^3$ stands for a group of the formula:

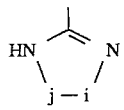

wherein
i is —O— or —S— and j is selected from the group consisting of a carbonyl group, a thiocarbonyl group, and an optionally oxidized sulfur atom or a group convertible thereto; or a salt thereof.

* * * * *

UNITED STATES PATENT AND TRADEMARK OFFICE
CERTIFICATE OF CORRECTION

PATENT NO.   : 5,496,835
DATED        : March 5, 1996
INVENTOR(S)  : Keiji KUBO et al.

It is certified that error appears in the above-indentified patent and that said Letters Patent is hereby corrected as shown below:

Column 46, line 52, change "N,N-lower" to --N,N-di-lower--
Column 47, line 15, change "elected" to --selected-- Column 48, line 35, change "1(acetyloxy)ethoxycarbonyl" to --1-(acetyloxy)ethoxycarbonyl-- ; line 36, change "tyryloxy)ethoxycarbonlyl," to --tyryloxy)ethoxycarbonyl,--; line 50, insert --wherein-- before "m is an integer".
Column 49, line 20, insert --,-- before "R$^1$";
to --formula:--

Signed and Sealed this

Eighth Day of October, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,496,835
DATED : March 5, 1996
INVENTOR(S) : Keiji KUBO et al.

It is certified that error appears in the above-indentified patent and that said Letters Patent is hereby corrected as shown below:

At Column 49, line 34, please change "formula," to read --formula:--.

Signed and Sealed this

Twenty-ninth Day of April, 1997

Attest:

BRUCE LEHMAN

Attesting Officer

Commissioner of Patents and Trademarks